United States Patent
Benkovic et al.

(10) Patent No.: US 10,973,835 B2
(45) Date of Patent: Apr. 13, 2021

(54) BORON-CONTAINING SMALL MOLECULES FOR INHIBITING ACTIVITY OF A RECEPTOR-LIKE PROTEIN TYROSINE PHOSPHATASE

(71) Applicant: The Penn State Research Foundation, University Park, PA (US)

(72) Inventors: Stephen J. Benkovic, State College, PA (US); Nicholas K. Tonks, Huntington, NY (US); Chun Yu Liu, Cary, NC (US); Navasona Krishnan, Cold Spring Harbor, NY (US); Chunliang Liu, Bellefonte, PA (US)

(73) Assignees: The Penn State Research Foundation, University Park, PA (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 15/910,677

(22) Filed: Mar. 2, 2018

(65) Prior Publication Data
US 2018/0258106 A1    Sep. 13, 2018

Related U.S. Application Data

(60) Provisional application No. 62/469,081, filed on Mar. 9, 2017.

(51) Int. Cl.
*A61K 31/69*   (2006.01)
*C07F 5/02*    (2006.01)

(52) U.S. Cl.
CPC ............. *A61K 31/69* (2013.01); *C07F 5/025* (2013.01); *C07F 5/027* (2013.01)

(58) Field of Classification Search
CPC ............ C07F 5/02; C07F 5/025; A61K 31/69
(Continued)

(56) References Cited

U.S. PATENT DOCUMENTS 7,582,621 B2   9/2009   Baker et al.
7,947,663 B2   5/2011   Adams et al.
(Continued)

FOREIGN PATENT DOCUMENTS

WO   WO-2004056322 A2 *   7/2004   ............... C07F 5/02

OTHER PUBLICATIONS

Hofer et al, Bioorg. Med. Chem. 2013, vol. 21, pp. 3203-3213.*
(Continued)

*Primary Examiner* — Craig D Ricci
*Assistant Examiner* — Janet L. Coppins
(74) *Attorney, Agent, or Firm* — Husch Blackwell LLP

(57) ABSTRACT

A method is disclosed for altering the redox equilibrium of a transmembrane receptor-like protein tyrosine phosphatase (RPTP), particularly a type IIa RPTP, by chemically modulating the activity through contact of such an enzyme with a diaryl boron compound that preferentially reacts with an RPTP in an oxidized state (CyS-OH). This redox modulation is most readily observed and put to use by assaying the inhibition of the phosphatase activity of the RPTP. Such an assay can be carried out on an enzyme in vitro or by contacting the enzyme in a living organism (in vivo). A useful diaryl boron compound corresponds in structure to Formula I in which Ar-1, (Continued)

Ar-2, $R^1$, $R^2$, $R^3$ and $R^4$ are defined within. A pharmaceutical composition containing a useful diaryl boron compound is also disclosed, as are particularly preferred diaryl boron compounds.

5 Claims, 4 Drawing Sheets

(58) Field of Classification Search
USPC .......................................................... 514/64
See application file for complete search history.

(56) References Cited

U.S. PATENT DOCUMENTS

| 8,980,544 B2 | 3/2015 | Benkovic et al. |
| 9,309,508 B2 | 4/2016 | Benkovic et al. |
| 2007/0286822 A1 | 12/2007 | Sanders et al. |

OTHER PUBLICATIONS

Ito et al., *Synlett*, 2003(10):1453-1458 (2003).
Hofer et al., *Bioorg Med Chem* 21(11):3202-3213 (2013).
Liu et al., *J Am Chem Soc* 135(39):14544-14547 (2013).
ISR-Written Opinion PCT/US2018/020701 (WO 2018/164959).

* cited by examiner

| Agrin (10 nM) | WT-LAR | | DA-LAR | | CS-LAR | |
| --- | --- | --- | --- | --- | --- | --- |
| Time (min) | 5 | 10 | 5 | 10 | 5 | 10 |

MuSK

Supernatant

Input

BORON-CONTAINING SMALL MOLECULES FOR INHIBITING ACTIVITY OF A RECEPTOR-LIKE PROTEIN TYROSINE PHOSPHATASE

CROSS-REFERENCE TO RELATED APPLICATION

This application claims priority from U.S. application Ser. No. 62/469,081 filed on Mar. 9, 2017, whose disclosures are incorporated by reference.

STATEMENT REGARDING FEDERALLY SPONSORED RESEARCH OR DEVELOPMENT

This invention was made with government support under Grant No. GM055989, awarded by the National Institutes of Health. The government has certain rights in this invention.

BACKGROUND ART

Reactive oxygen species (ROS) such as peroxides and hydrogen peroxide are tightly controlled byproducts generated from mitochondrial electron transport chains and various enzymatic reactions. [Paulsen et al., *Chem. Rev.* 2013, 113:4633-4679.] Under the right condition, ROS can function as second messengers for signal transduction by modifying cysteine residues on proteins, inducing changes to the structure, conformation, and activity of the modified proteins. [Winterbourn, *Nat. Chem. Biol.* 2008, 4:278-286; D'Autreaux et al., *Nat. Rev. Mol. Cell. Bio.* 2007, 8:813-824; Poole, *Free Radic. Biol. Med.* 2015, 80:148-157; Mailloux et al., *Redox Biol.* 2014, 2:123-139; Tonks, *Cell* 2005, 121:667-670; Meng, et al., *Mol. Cell* 2002, 9:387-399; Tonks, *Nat. Rev. Mol. Cell Biol.* 2006, 7:833-846.]

In the presence of reactive oxygen species, two electron oxidation of a cysteine residue generates a sulfenic acid (Cys-SOH) as the initial product, which can lead to disulfide, S-glutathiolation, S-nitrosation, thiosulfinate, sulfinic acid, sulfonic acid, and sulfenamide formation. [Paulsen et al., *Chem. Rev.* 2013, 113:4633-4679; Mailloux et al., *Redox Biol.* 2014, 2:123-139; Salmeen et al., *Nature* 2003, 423: 769-773.]

Specifically, the reversible nature of cysteine oxidation makes it suitable for regulating a wide array of processes such as signal transduction, managing the intracellular redox state, modulating gene transcription, and catalysis. [Paulsen et al., *Chem. Rev.* 2013, 113:4633-4679; Winterbourn, *Nat. Chem. Biol.* 2008, 4:278-286; Poole, *Free Radic. Biol. Med.* 2015, 80:148-157; Barford, *Opin. Struct. Biol.* 2004, 14:679-686; Roos, et al., *Free Radical Biol. Med.* 2011, 51:314-326; Salmeen et al., *Nature* 2003, 423:769; Jacob et al., *Chem. Res. Toxicol.* 2012, 25:588-604.] Therefore, post-translational cysteine redox modification is becoming an increasingly important feature for therapeutic focus [Wani et al., *Front. Pharmacol.* 2014, 5:1-8; Jacob et al., *Chem. Res. Toxicol.* 2012, 25:588-604], with growing recognition of the implications of cysteine redox regulation in treating cancer [Seo et al., *Proc. Natl. Acad. Sci. USA* 2009, 106:16163-16168; Anastasiou et al., *Science* 2011, 334:1278-1283; Lou et al., *FEBS J.* 2007, 275:69-88.], heart disease [Svoboda et al., *Circ. Res.* 2012, 111:842-853; Go et al., *Free Radic. Biol. Med.* 2011, 50:495-509], diabetes [Goldstein et al., *Diabetes* 2005, 54:311-321; van Montfort et al., *Nature* 2003, 423: 773-777; Tonks, *Nat. Rev. Mol. Cell Biol.* 2006, 7:833-846], inflammation, [Yang et al., *J. Leukoc. Biol.* 2013, 93:865-873] and neural diseases [Canet-Aviles et al., *Proc. Natl. Acad. Sci. USA* 2004, 101:9103-9108; Gu et al., *Science* 2002, 297:1186-1190].

One prominent target of cysteine redox regulation is the protein tyrosine phosphatase (PTP) superfamily, which is a vital component of cellular signaling networks. PTPs are a popular drug target for many human diseases. [Takahashi et al., *Trends Neurosci.* 2013, 36, 522-534; Tonks, *FEBS J.* 2013, 280:346-378.] The activity of PTPs can be regulated through a reversible cysteine redox reaction [Paulsen et al., *Chem. Rev.* 2013, 113:4633-4679; Winterbourn, *Nat. Chem. Biol.* 2008, 4, 278-286; D'Autreaux et al., *Nat. Rev. Mol. Cell. Bio.* 2007, 8:813-824; Poole, *Free Radic. Biol. Med.* 2015, 80:148-157; Tonks, *Cell* 2005, 121:667-670].

More than half of the classical PTP genes in humans encode transmembrane receptor-like PTPs (RPTPs) proteins, which are involved in important developmental processes such as the formation of the nervous system. [Mohebiany et al., *FEBS J.* 2013, 280:388-400.] The RPTPs are a large protein family with eight subtypes based on diverse extracellular domains [Takahashi et al., *Trends Neurosci.* 2013, 36(9):522-534].

Some RPTPs such as the type IIa RPTPs contain extracellular immunoglobulin-like and fibronecin type III domains that are modified by alternative splicing. These motifs are commonly found in cell adhesion molecules, suggesting a potential role in cell-cell and cell-matrix interactions [Tonks, *FEBS J.* 2013, 280:346-378].

The type IIa RPTPs also contain two intracellular protein tyrosine phosphatase (PTP) domains, the membrane-proximal D1 domain with robust catalytic activity and the membrane-distal D2 domain with residual or no catalytic activity. The PTP domains are linked to the extracellular domains via a transmembrane portion [Takahashi et al., *Trends. Neurosci.* 2013, 36(9):522-534.]

The type IIa RPTPs are composed of three members in vertebrates: leukocyte common antigen-related (LAR), PTPσ [PTP sigma], and PTPδ [PTP delta]. The activity of these RPTPs is also subjected to regulation (inhibition) through a cysteine redox reaction. [Cook et al., *Free Radic. Biol. Med.* 2016, 90:195-205; Jeon et al., *Mol. Cells* 2013, 36:55-61.]

Recent studies have implicated over expression or enhanced activity of LAR in several clinically relevant conditions. Included among those conditions are Type 2 diabetes and several cancerous conditions.

For example, Zabolotny et al., *Proc. Natl. Acad. Sci., USA,* 2001, 98(9):5187-5192, reported that overexpression of LAR in transgenic mouse muscle causes whole-body insulin resistance, most likely due to dephosphorylation of specific regulatory phosphotyrosines on insulin receptor substrate 1 (IRS-1) proteins. Those authors concluded that their data suggested that increased expression and/or activity of LAR or related PTPs in insulin target tissues of obese humans may contribute to the pathogenesis of insulin resistance as is found in Type 2 diabetes. More recently, Gorgani-Firuzjaee et al., *J. Endocrinol.* 2012, 215:71-77, reported that palmitate-induced LAR in myotubes of cultured mouse C2C12 (myoblast) cells reduced insulin-stimulated glucose uptake compared to control and LAR knockdown cells.

LAR may also affect carcinogenesis. LAR gene amplification and mutation have been reported in human cancers such as small-cell lung carcinoma and colon cancer [Andersen et al., *FASEB J* 2004, 18:8-30; Harder et al., *Genomics* 1995, 27:552-553; Wang et al., *Science* 2004, 304:1164-1166]. In addition, LAR expression is significantly increased in thyroid carcinomas [Konishi et al., *Br J Cancer* 2003, 88:1223-1228] and breast cancer [Yang et al., *Mol Carcinog* 1999, 25:139-149], especially in breast cancer tissues with metastatic potential.

Another type IIa RPTP, PTP-sigma (PTPσ) is involved in modulating the PTK signaling pathway and repair of damaged spinal cord. More specifically, studies by several groups such as Dyck et al., *Stem Cells*, 2015, 33:2550-2563, indicate that post-injury neural repair is inhibited by chondroitin sulfate proteoglycans (CSPGs) whose activity is modulated by PTP as well as LAR. The effectiveness of the CSPGs in inhibiting regrowth can be lessened by lessening the activity of the RPTPs. Others report that PTPσ regulates hematopoietic stem cells (HSCs) functional capacity via RAC1 inhibition and suggest that selecting for PTPσ-negative human HSCs may be an effective strategy for enriching human HSCs for transplantation. [Quarmyne et al., *J. Clin. Invest.* 2015, 125(1):177-182.]

A mechanistic unifying characteristic of the type IIa RPTP molecules is that on oxidation, these molecules form sulfenic acids (S—OH) rather than cyclic sulenamides as is the case for other RPTP molecules such as the enzyme PTP1B. An oxidized, sulfenic acid form of a type IIa RPTP can be reversibly-trapped and its activity reversibly-inhibited by a boron-containing compound described hereinafter.

The sulfenic acid (Cys-OH; oxidized) form of a type IIa RPTP is in equilibrium with the unoxidized, thiol (CysH) form. The oxidation is caused by a cell's production of ROS and the reduction is carried out by glutathione, $H_2S$ or other cellularly-formed reductant. The reduced form is the active form of the phosphatase, whereas the oxidized form is the inactive form. Thus, the enzyme's substrate is dephosphorylated by the active enzyme and remains phosphorylated in the presence of the inactive form.

The RPTPs also interact in the synapse, primarily on the presynaptic side, but also on the postsynaptic side, to make trans-synaptic adhesion complexes with multiple postsynaptic binding partners to regulate synapse organization and stability. These RPTPs bind to overlapping sets of postsynaptic partners, forming "hubs" in a manner similar to that of neurexin, that assist synapse organization. Multiple RPTP complexes have been identified that participate in excitatory synapse development, whereas only PTPδ is specific for inhibitory synapses. [Takahashi et al., *Trends. Neurosci.* 2013, 36(9):522-534.]

RPTPs in trans-synaptic complexes have three general functions in synaptic organization: one is to mediate cell-cell adhesion at synapses; a second is to mediate presynaptic differentiation, local recruitment of synaptic vesicles and release and recycling machinery; and the third is to trigger postsynaptic differentiation, local recruitment of neurotransmitter receptors, scaffolds, and signaling proteins, a form of anterograde synaptogenic signaling triggered by binding of the presynaptic RPTP to dendritic binding partners. [Takahashi et al., *Trends. Neurosci.* 2013, 36(9):522-534.]

Similarly, the RPTPs have an important role in formation and stabilization of neuromuscular junctions (NMJs). Formation of NMJs involves a complex signaling process, both spatially and temporally, between motor neurons and muscle myotubes, the end result of which is the clustering of acetylcholine receptors (AChRs) on the postsynaptic side of the junction and a differentiated nerve terminal on the presynaptic side. These effects have been shown in fruit flies and in chick embryo neurodevelopment. [Stepanek et al., *J. Neurosci.* 2005 25(15):3813-3823.] Muscle-specific kinase (MuSK) plays an important role on the postsynaptic side. [Hubbard et al., *Biochim. Biophys. Acta*, 2013, 1834(10): 2166-2169.]

Also involved in formation of NMJs, are a neuronally-derived heparin-sulfate proteoglycan, agrin, and three muscle proteins: low-density lipoprotein receptor-related protein-4 (LRP-4), downstream kinase-7 (Dok7) and rapsyn. Failure to form proper NMJs (lack of NMJs is lethal), or to maintain them, leads to neuromuscular-transmission pathologies such as myasthenia gravis and congenital myasthenic syndromes (CMS). [Hubbard et al., *Biochim. Biophys. Acta*, 2013, 1834(10):2166-2169.]

MuSK is activated by phosphorylation of six of its nineteen tyrosine residues. [Watty et al., *Proc. Natl. Acad. Sci., U.S.A.,* 2000, 97(9):4585-4590.] Increasing MuSK activity delays denervation and improves motor function in amyotrophic lateral sclerosis (ALS) mice [Perez-Garcia et al., *Cell Reports* 2012, 2:497-502.] Thus, inhibiting a correct phosphatase could be useful in treating ALS.

Although PTPs have garnered substantial attention as potential therapeutic targets, there are several profound challenges. One of the challenges so far has been developing an inhibitor with sufficiently high specificity, because there is a high degree of amino acid sequence similarity surrounding the active site of PTPs [Tonks, *FEBS J.* 2013, 280:346-378]. Therefore, the common tactic of looking for inhibitors based on their active site structure has not yielded much success. Moreover, the highly charged active site of the enzymes, coupled with their susceptibility to oxidation, has further contributed to the view of PTPs as being challenging, "undruggable" targets [Tonks, *Cell* 2005, 121:667-670; Tonks, *FEES J.* 2013, 280:346-378].

In recent years, boron based compounds have found numerous useful applications in molecular signaling, biotechnology, and therapeutic treatments [Liu et al., *Bioorg. Med. Chem.* 2014, 22:4462-4473]. One unique property of boron compounds is their ability to switch between the trigonal and tetrahedral geometry depending on what is bound to the boron atom. For example, the neutral form of boronic acid adopts a planar trigonal geometry, whereas the conjugate base (anionic) is tetrahedral. This structural and electronic versatility imbues boron-based compounds with reactivity to the target protein, as well as flexibility to modulate parameters such as pharmacokinetic and bioavailability.

Recent studies have found boronic acids and benzoxaboroles to be capable of trapping sulfenic acids by forming a covalent S—O—B bond [Liu et al., *J. Am. Chem. Soc.* 2013, 135:14544-14547]. In fact, arylboronic acids were found to be slow binding competitive inhibitors for enzymes that require a catalytic sulfenic acid for the enzymatic activity [Martinez et al., *J. Am. Chem. Soc.* 2014, 136:1186-1189].

As is discussed and illustrated hereinafter, the present invention utilizes different boron-containing compounds (not limited to boronic acids and borinic acids) to inhibit the activity of a different group of enzymes from those disclosed in Liu et al., *J. Am. Chem. Soc.* 2013, 135:14544-14547, the latter being located in the cytosol of normal cells and for EGFR, also in the membrane of cancerous renal cells. Indeed, the boronic acid compounds described by Liu et al. are substantially inactive in inhibiting the enzymes discussed herein.

BRIEF SUMMARY OF THE INVENTION

The present invention contemplates a method of chemically modulating the activity of a transmembrane receptor-like protein tyrosine phosphatase (RPTP), particularly a type IIa RPTP, by altering the redox equilibrium by contacting such an enzyme with a boron compound that preferentially targets an RPTP in an oxidized state (CyS-OH). This redox modulation is most readily observed and put to use by assaying the inhibition of the phosphatase activity of a RPTP. Such an assay can be carried out on an enzyme in vitro or by contacting the enzyme in a living organism (in vivo).

Thus, put differently, the present invention contemplates a method of inhibiting the phosphatase activity of a RPTP, particularly a type IIa RPTP, that comprises the steps of contacting a RPTP with an effective amount of a boron-containing compound of Formula I, and maintaining that contact for as long a time period as desired to inhibit that phosphatase activity

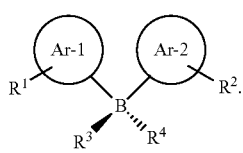

I

In Formula I, the circled substituents Ar-1 and Ar-2 bonded to the boron atom, B, are the same or different aromatic substituent that is carbocyclic or heterocyclic, contains one ring, two or three fused rings, and when heterocyclic, contains up to four nitrogen atoms in the ring or rings, or one oxygen and up to three nitrogens in the ring or rings.

$R^1$ and $R^2$ are the same or different substituents the sum of whose Hammett sigma functions for para ($\sigma_p$) and/or meta ($\sigma_m$) substituents, as appropriate, is greater (more positive) than about zero. $R^3$ and $R^4$ are (a) both fluoride, the depicted boron atom has a negative charge (B$^-$) and a charge-balancing pharmaceutically acceptable cation (Mt) is present, or (b) $R^3$ is OH and $R^4$ is absent.

In a compound of Formula I, and in the formulas to follow, Ar-1 and Ar-2 are independently selected. Preferred substituents from which Ar-1 and Ar-2 selected are phenyl, which is particularly preferred for both Ar-1 and Ar-2, as well as 1- or 2-naththyl, pyridyl, pyrazinyl, indoyl, quinolinyl, qunioxylinyl, purinyl and pyrimidinyl. Further exemplary Ar-1 and Ar-2 groups are illustrated hereinafter.

Further, in such a compound, $R^1$ and $R^2$ are the same or different substituents that are selected from the group consisting of hydrogen, halogen, $C_1$-$C_6$-hydrocarbyl, trifluoromethyl, cyano, nitro, phenyl, N-morpholinyl, N-piperidinyl, 4-cyanophenoxy, benzoyl, $C_1$-$C_6$-hydrocarboyl, $C_1$-$C_6$-hydrocarbyloxy-carbonyl, carbamoyl, mono- and di-$C_1$-$C_6$-hydrocarbyl carbamoyl, sulfamoyl, mono- and di-$C_1$-$C_6$-hydrocarbyl sulfamoyl, and optionally substituted phenyl and benzoyl. An optional substituent is selected from the $R^1$ and $R^2$ substituents other than hydrogen, phenyl and benzoyl, with the proviso that the sum of Hammett sigma functions for para ($\sigma_p$) and/or meta ($\sigma_m$) substituents, as appropriate, of the depicted $R^1$ and $R^2$ groups is greater than about zero.

The phrase "the sum of Hammett sigma functions for para and/or meta substituents as appropriate is greater than about zero" is used to mean that the Hammett sigma function values of the $R^1$ and $R^2$ substituents are added to each other. If both substituents are substituted in the para position on the ring relative to the boron atom, the sigma function values for the para positions are used for the sum. If both are in the meta position relative to the boron atom, two meta position values are used. When the rings are substituted in the para position for one and meta position for the other substituent, the respective para and meta position values are used for the sum. Also, "greater than about zero" is used to mean more positive than about zero.

It is to be understood that in some substituent rings a para and/or meta position may not be available for substitution. In that instance, the Hammett sigma function value for a para substituent is selected where that substituent can donate or withdraw electron density by a resonance effect, and a meta value is used where electron density donation or withdrawal can be exerted only by inductive effect.

It is particularly preferred that at least one of Ar-1 and Ar-2 is phenyl. With Ar-2 being phenyl as illustrative, a boron-containing compound is a compound of Formula Ia

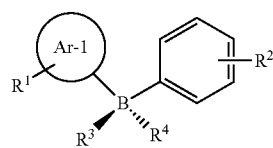

Ia wherein Ar-1, $R^1$, $R^2$, $R^3$ and $R^4$ are as defined previously.

More preferably, both of Ar-2 and Ar-1 are phenyl, in which case the boron-containing compound is a compound of Formula Ib

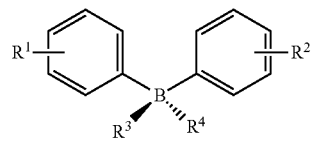

Ib wherein $R^1$, $R^2$, $R^3$ and $R^4$ are as defined previously.

In some preferred embodiments, one or both of $R^1$ and $R^2$ is a halogen. In others, one of $R^1$ and $R^2$ is a halogen such as chloro or fluoro, and the other is phenyl.

The two structural variants described above as constituting sub-generic compounds of Formula I are illustrated below as compounds of Formulas II and III, and in which Ar-1, Ar-2, $R^1$ and $R^2$ have the previously defined meaning in each formula.

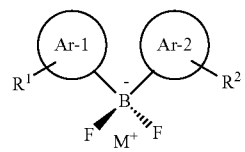

II where M$^+$ is a pharmaceutically acceptable cation; and

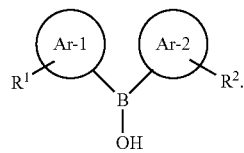

III

As was the case for a compound of Formula I, phenyl is a preferred boron-bonded Ar-1 and Ar-2 substituent of a compound of Formulas II and III, so that preferred compounds of Formulas II and III have structural Formulas IIa, IIb, IIIc and IIIb shown below, wherein M+, $R^1$ and $R^2$ are as defined previously.

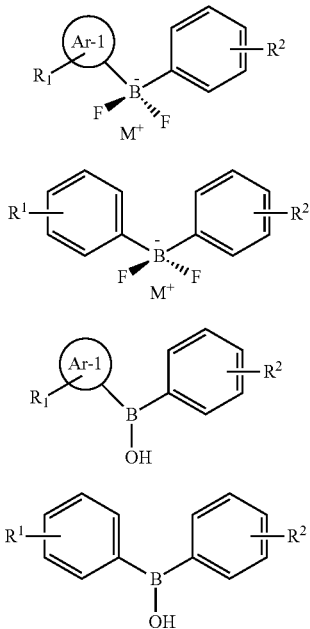

IIa

IIb

IIIa

IIIb

Particular compounds of Formula IIb and Formula IIIb are also contemplated. The phenyl rings of these particular compounds contain $R^1$ and $R^2$ substituents that different from each other. It is particularly preferred that one of $R^1$ and $R^2$ is phenyl and the other is halogen.

Also contemplated is a pharmaceutical composition comprising a pharmaceutically acceptable diluent in which is dissolved or dispersed a RPTP activity-inhibiting amount of a compound of Formula I

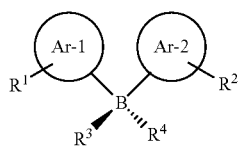

I wherein Ar-1 and Ar-2, $R^1$, $R^2$, $R^3$ and $R^4$ are as defined previously. A pharmaceutical composition containing a compound of Formulas Ia, Ib, II, IIa, IIb, III, IIIa and IIIb is also contemplated.

Yet another contemplated aspect of the invention is a method of inhibiting the phosphatase activity of a RPTP, and particularly a type IIa RPTP, that comprises the steps of contacting that RPTP with an effective amount of a boron-containing compound of Formula IV, and maintaining that contact for as long a time period as' desired to inhibit that phosphatase activity. In Formula IV, $R^6$ has a Hammett sigma function value for a para ($\sigma_p$) and/or a meta ($\sigma_m$)

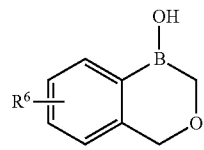

IV substituent, as appropriate, that is about −0.9 to about +0.08, preferably about −0.7 to about 0.00. The electron donating substituents from which $R^6$ is chosen typically are amines such as amino, mono- and di-$C_1$-$C_6$-hydrocarbylamino, and cyclic amino having $C_5$-$C_7$-ring atoms, including the amino nitrogen atom such as N-pyrrolidinyl, N-morpholinyl, and N-piperidinyl groups and the like; straight, branched and cyclic $C_1$-$C_8$-hydrocarbyl groups such as methyl, ethyl, 2-ethylhexyl, allyl, but-3-en-2-yl, cyclopentyl, cyclohexyl, benzyl and phenyl groups and the like; and straight, branched and cyclic $C_1$-$C_8$-hydrocarbyloxy groups such as methoxy, ethoxy, allyloxy, but-3-en-2-yloxy, cyclopentyloxy, cyclohexyloxy, benzyloxy and phenyloxy groups and the like.

A pharmaceutical composition is also contemplated that comprises a pharmaceutically acceptable diluent in which is dissolved or dispersed a RPTP activity-inhibiting amount of a compound of Formula IV

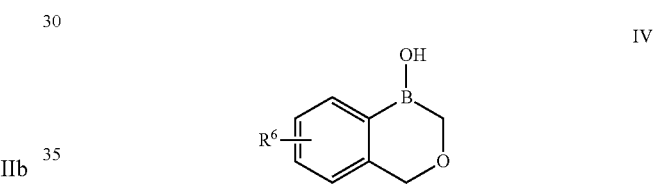

IV wherein $R^6$ is as defined above.

BRIEF DESCRIPTION OF THE DRAWINGS

In the Figures forming a portion of this disclosure.

DETAILED DESCRIPTION OF PREFERRED EMBODIMENTS

Figure 1:
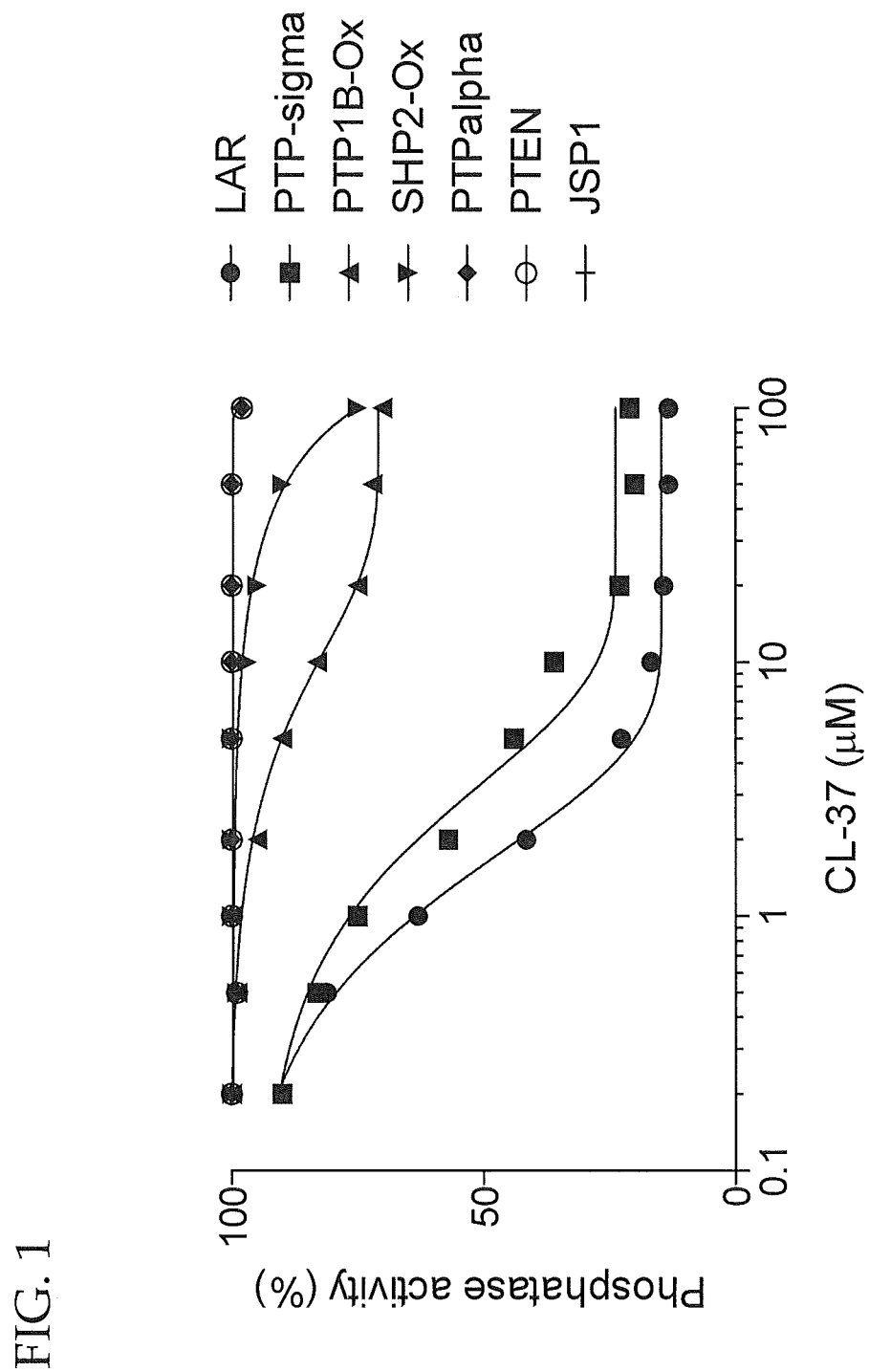
FIG. 1 is a graph showing the phosphatase activity at concentrations between 0.1 and 100 μM of Compound CL-37, whose structure is shown hereinafter, against several protein tyrosine phosphatase enzymes using the "Standard Assay Conditions" discussed hereinafter.

The following description illustrates a novel approach to chemically modulating the activity of RPTPs by altering the redox equilibrium of RPTPs through boron compounds that preferentially react with the oxidized state (Cys-OH) of a RPTP. We found the diarylborate (1) and 6-membered benzoxaboroles (2) to be very effective at trapping RPTPs in their oxidized (inactive) states. In contrast, several boronic acids and 5-membered benzoxaboroles (3) were ineffective at inhibiting the phosphatase activity of the RPTPs in the same experimental assay.

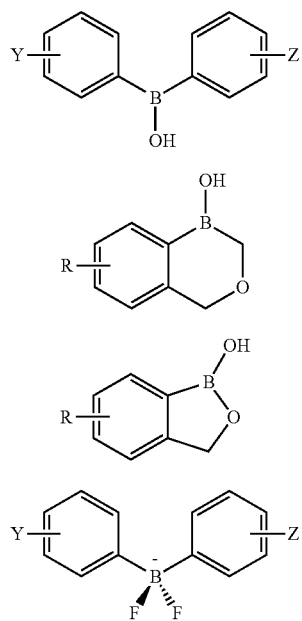

One particularly interesting class of diarylborates is the diaryldifluoroborate (4). No biological activities or applications have been found reported for the diaryldifluoroborates, partly due to a concern about the stability of the B—F bond. In fact, outside of a handful of reports on their use as intermediates/reagents for chemical syntheses of non-boron containing compounds [Ito et al., *Synlett*, 2003, 10, 1435-1438; Franzke et al., *Synthesis*, 2008, 2, 245-252; Mizuno et al., *Chem Commun*, 2006, 48, 5042-5044], there have been few inquiries into the utility of diaryldifluoroborates, particularly pharmaceutical and biological utilities.

As disclosed in detail hereinafter, we found the diarylfluoroborates are selective and potent (sub-μM) competitive inhibitors (better inhibitors than benzoxaborole 2) of RPTPs, such as PTPσ and LAR. Specifically, the diaryldifluoroborates selectively trap the oxidized RPTPs by reacting with the oxidized cysteine-SOH group in the active site, preventing the enzymes from reverting back to the reduced sulfhydryl state. The diaryldifluoro-borates were found to be very selective for the oxidized state of RPTPs, and had little effect on the reduced states of RPTPs. Also, we found the diarylfluoroborate compounds to be quite stable against hydrolysis in aqueous solution.

Once an oxidized RPTP is trapped by such a boron compound, the enzyme cannot easily be converted back to the reduced form, suggestive of the inhibitor being tightly bound to the enzyme. In other words, a contemplated boron compound offers a novel approach to inhibit these phosphatases by changing the equilibrium between the reduced (active) and oxidized (inactive) forms of the enzymes. This novel approach of inhibiting RPTP through selective modulation of the enzyme's redox equilibrium offers another layer of target-specificity over conventional inhibitor strategy. Furthermore, the diaryldifluoroborates are very stable under ambient conditions, can be prepared with high yield, and exhibit good resistance to hydrolysis in a highly aqueous environment.

Additionally, the diaryldifluoroborates were found to exhibit very selective targeting, and were unable to trap the oxidized states of some other PTPs, such as, PTEN, PTPα, and JSP1 (see, FIG. 1). The diaryldifluoroborates exhibited some ability to trap the oxidized PTP1B and SHP2, but the inhibitory activity (i.e. $IC_{50}$) was at least 2-3 orders of magnitudes lower as compared to the effect on LAR or PTPσ. Structural reactivity studies showed that the diaryl moiety is important to the inhibitory activity on RPTPs. A compound exhibiting an inhibitory activity, $IC_{50}$, that is 2 or more orders of magnitude greater (poorer inhibitor) for a given PTP as compared to that exhibited for LAR or PTPα under the same assay conditions is deemed not to be an inhibitor of that given PTP enzyme.

Furthermore, unlike the trend observed in the boronic acids binding to Fries acid [Liu et al., *J. Am. Chem. Soc.* 2013, 135, 14544-14547], increasing the electrophilicity on the boron atom increases the inhibitory activity of diaryldifluoroborates on RPTPs. Therefore, the diarylborates, especially the diaryldifluoroborates, offer a novel approach to selectively inhibiting the reduction, thus the reactivation, of oxidized RPTPs.

It should be noted that most protein cysteine SH groups react slowly with peroxide (second order rate constant about 20 $M^{-1}s^{-1}$) [Winterbourn et al., *Free Radio. Biol. Med.*, 2008, 45, 549-556] to generate the corresponding sulfenic acid (Cys-SOH), which is relatively labile and can undergoes numerous side reactions [Paulsen et al., *Chem. Rev.*, 2013, 113, 4633-4679; D'Autreaux et al., *Nat. Rev. Mol. Cell. Bio.*, 2007, 8, 813-824].

The cysteine sulfenic acid can also be further oxidized into sulfinic ($Cys-SO_2H$) or sulfonic ($Cys-SO_3H$) acids, leading to the proteins being irreversibly deactivated, and these modifications are often associated with oxidative stress [Mailloux et al., *Redox Biol.*, 2014, 2, 123-139; Murphy, *Antioxid. Redox Signal*, 2012, 16, 476-495]. Thus, another potential utility of this boron-based approach to modulate protein's cysteine redox equilibrium can include protection from irreversible over-oxidation of the protein.

Monitoring the oxidation of a cysteine sulfur atom can be difficult and time-consuming. Assaying the inhibition of phosphatase activity can usually be carried out quickly and easily. In addition, because of the importance of the role of RPTP enzymes in health-related biological processes, phosphatase inhibition of the membrane-bound PTP enzymes can be of medical importance.

Thus, the present invention contemplates a method of inhibiting the phosphatase activity of a RPTP that comprises the steps of contacting a membrane-bound RPTP with an effective amount of a boron-containing multi-component compound of Formula I, and maintaining that contact for as long a time period as desired to inhibit the phosphatase activity.

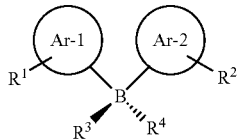

I

In Formula I, the circled substituents Ar-1 and Ar-2 bonded to the boron atom, B, are the same or different aromatic substituent that is carbocyclic or heterocyclic, contains one ring, or two or three fused rings, and when heterocyclic, contains up to four nitrogen atoms in the ring or fused rings, or one oxygen and up to three nitrogen atoms in the ring or fused rings.

$R^1$ and $R^2$ are the same or different substituents the sum of whose Hammett sigma function values for para and/or meta substituents as appropriate is greater (more positive) than about zero.

In one embodiment, $R^3$ and $R^4$ of Formula I are both fluoride, the depicted boron atom has a negative charge ($B^-$) and a charge-balancing pharmaceutically acceptable cation ($M^+$) is present. Such a sub-component compound can be illustrated by Formula II.

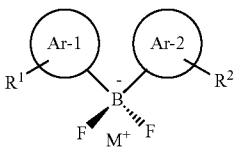

II

In another embodiment, $R^3$ is OH and $R^4$ is absent. A sub-component compound of this embodiment is illustrated by Formula III

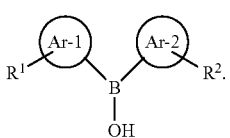

III

In a compound of each of Formulas I, II and III, it is preferred that at least one of Ar-1 and Ar-2 be phenyl, thereby further defining structural formulas Ia, IIa and IIIa, below. In many

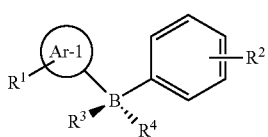

Ia

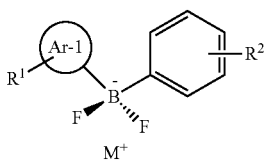

IIa

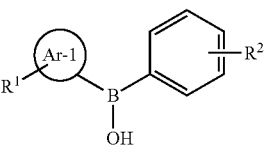

IIIa embodiments, it is preferred that both Ar-1 and Ar-2 be phenyl, thereby further defining structural formulas Ib, IIb and IIIb, below.

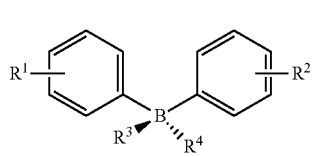

Ib

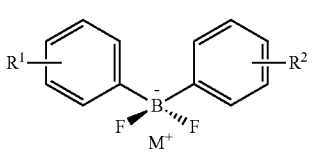

IIb

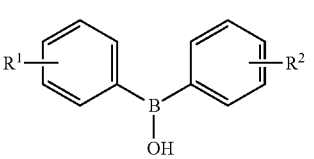

IIIb

In a compound of Formulas I, II and III, $R^1$ and $R^2$ are the same or different substituents that are selected from one or more of the group consisting of hydrogen, halogen, $C_1$-$C_6$-hydrocarbyl, trifluoromethyl, cyano, nitro, phenyl, optionally substituted phenyl, benzoyl, optionally substituted benzoyl, $C_1$-$C_6$-hydrocarbyloxycarbonyl, carbamoyl, mono- and di-$C_1$-$C_6$-hydrocarbyl carbamoyl, sulfamoyl, mono- and di-$C_1$-$C_6$-hydrocarbyl sulfamoyl. An optional phenyl or benzoyl substituent is selected from the $R^1$ and $R^2$ substituents other than hydrogen, phenyl and benzoyl.

In addition, the sum of Hammett sigma function values for para and/or meta substituents of the $R^1$ and $R^2$ groups as appropriate is greater (more positive) than about zero. More preferably, the sum of the Hammett sigma function values for the $R^1$ and $R^2$ substituents is greater than about +0.1.

Without wishing to be bound by theory, based on the observed inhibition data, it is believed that a more positive sum of the Hammett sigma values causes the boron atom to become relatively more electrophilic and a better receptor for the enzyme's oxidized PTP sulfur-oxygen ligand. This is not to say that that sum is the only factor involved in the interaction of a contemplated compound of Formula I and a binding partner target RPTP enzyme. Steric as well as hydrophobic and hydrophilic factors likely also contribute to the interaction.

Hammett sigma function values for substituents are found throughout the chemical literature. One extensive list is provided in Hansch et al., *Chem. Rev.* 1991, 165-195. Another, shorter, table is found in Hine, *Physical Organic Chemistry*, 2nd ed., McGraw-Hill Book Company, Inc., New York, 1962, page 87. As can be readily seen from examination of the table in Hine, Hammett sigma values range from about minus 1 (−1.0) to about plus 1.9 (+1.9), thereby placing lower and upper limits on the range of summed sigma values of about −2.0 to about +3.8, respectively.

The phrase "the sum of Hammett sigma function values for para and/or meta substituents as appropriate is greater than about −0.2" is used to mean that the Hammett sigma function values of the $R^1$ and $R^2$ substituents are added to each other. If both substituents are substituted in the para position on the ring relative to the boron atom, the sigma function values for the para positions are used for the sum. If both are in the meta position relative to the boron atom, two meta position values are used. When the rings are substituted in the para position for one and meta position for the other substituent, the respective para and meta position values are used for the sum.

Illustrative results that generally correlate the Hammett sigma function values for para substituents in a compound of Formula II are shown in Table 1, below, where $R^1$ and $R^2$ are para to the boron atom and the compound used was a potassium salt. The data of Table 1 show that having a negative value for the sum of the sigma value (para) resulted in poor inhibition.

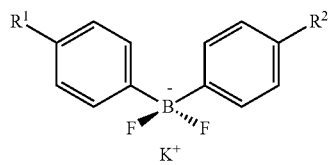

TABLE 1*

| Compound Number | $R^1$ and $R^2$ | Sum of $\sigma_p$ values | LAR-ox Ki (μM) |
|---|---|---|---|
| CL60 | OCH$_3$, OCH$_3$ | −0.54 | >1000 |
| CL37 | H, H | 0.00 | 5 |
| CL61 | Cl, Cl | +0.46 | 4 |
| CL65 | F, F | +0.12 | 4 |
| CL76 | F, Phenyl | 0.05 | 1 |
| CL83 | Cl, Phenyl | +0.22 | 3 |

*Data obtained as discussed hereinafter.

In some preferred embodiments of a contemplated method, one or both of $R^1$ and $R^2$ is a halogen such as chloro or fluoro. In others, one of $R^1$ and $R^2$ is a halogen such as chloro or fluoro, and the other is phenyl.

Illustrative results that generally correlate inhibitory activity with the Hammett sigma function values for para substituents ($\sigma_p$) in a compound of Formula III are shown in Table 2, below, where $R^1$ and $R^2$ are para to the boron atom bond.

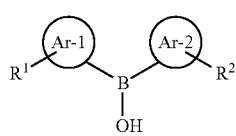

III

TABLE 2*

| Compound Number | $R^1$ and $R^2$ | Sum of $\sigma_p$ values | LAR-ox Ki (μM) |
|---|---|---|---|
| CL30 | H, H | 0.00 | 20 |
| CL73-2 | F, Phenyl | 0.05 | 1 |
| CL82 | Cl, Phenyl | +0.22 | 0.3 |

*Data obtained as discussed hereinafter.

For a compound of Formulas II and III, Ar-1 and Ar-2 are both preferably phenyl. However, as noted above, each can independently be a carbocyclic or heterocyclic aromatic substituent. The aromatic ring contains one ring, or two or three fused rings, and when heterocyclic, contains up to four nitrogen atoms in the ring or fused rings, or one oxygen and up to three nitrogens (zero to three) in the ring or fused rings. Each of the Ar-1 and Ar-2 substituents can themselves be substituted with $R^1$ and $R^2$ substituents as discussed previously.

Illustrative Ar-1 and Ar-2 substituents include phenyl, which is particularly preferred, 1- or 2-naththyl, pyridyl, pyrazinyl, indoyl, quinolinyl, qunioxylinyl, purinyl and pyrimidinyl. Structural formulas for those and additional substituents are shown below and in which the line extending from within a ring that is crossed by a dotted line indicates a bond to boron that can be at any available position in a depicted ring. $R^1$ and $R^2$ substituents are not shown below for increased clarity.

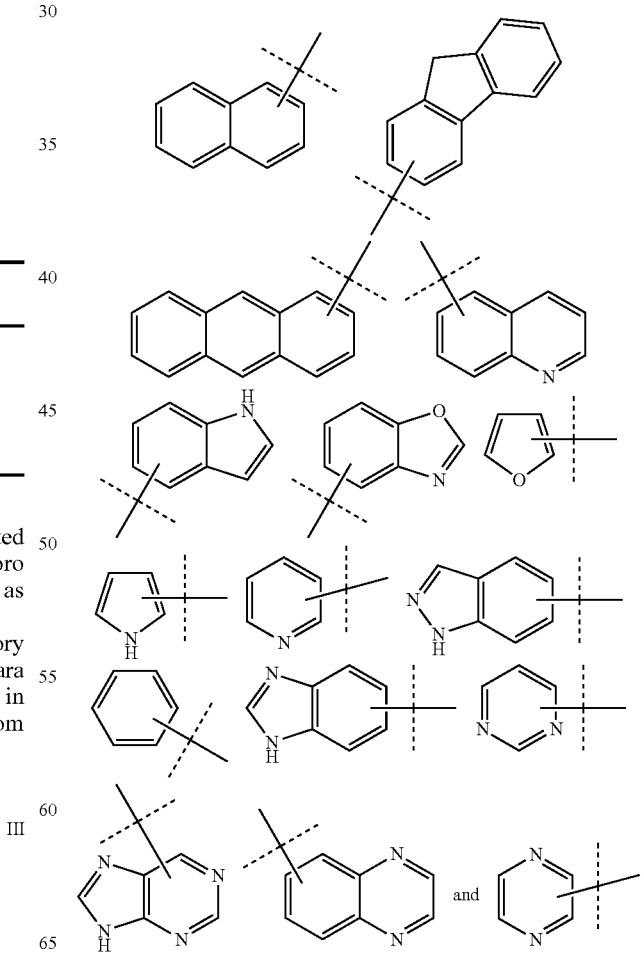

Particular compounds of Formula IIb and Formula IIIb are also contemplated. The phenyl rings of these particular compounds contain previously defined $R^1$ and $R^2$ substituents, that are different from each other. It is particularly preferred that one of $R^1$ and $R^2$ is phenyl and the other is halogen.

Two particularly preferred compounds of Formula IIb are shown below and are designated herein as Compounds CL-76 and CL-83, in which $M^+$ is a pharmaceutically acceptable cation, preferably potassium.

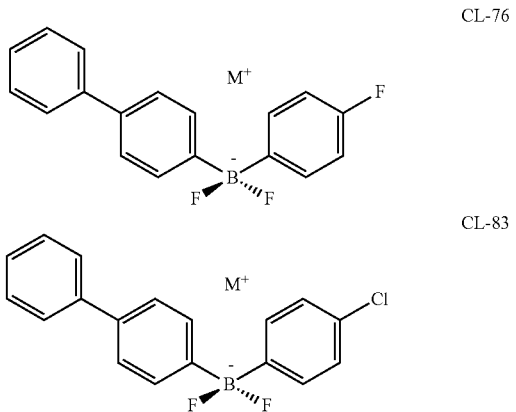

CL-76

CL-83

Two particularly preferred compounds of Formula IIIb are shown below and are designated herein as Compounds CL-73-2 and CL-82.

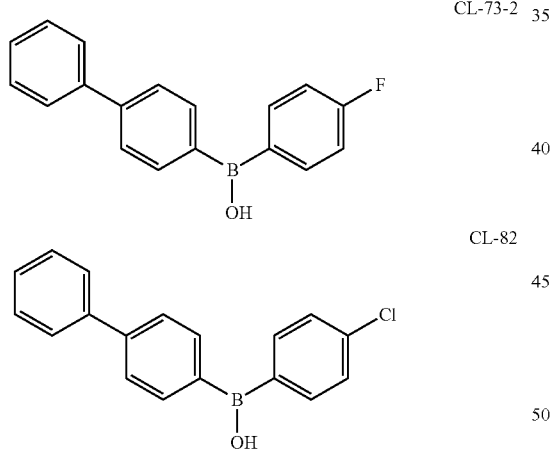

CL-73-2

CL-82

Also contemplated is a pharmaceutical composition comprising a pharmaceutically acceptable diluent in which a RPTP phosphatase activity-inhibiting amount of a compound of Formula I is dissolved or dispersed,

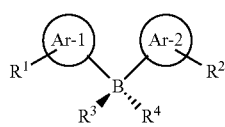

I wherein Ar-1 and Ar-2 are as previously defined, and $R^1$ and $R^2$ are the same or different substituents the sum of whose Hammett sigma functions for para and/or meta substituents, as appropriate, is greater than about −0.2, preferably greater than about 0.0, and most preferably greater than about 0.1.

In one embodiment, $R^3$ and $R^4$ are both fluoride, the depicted boron atom has a negative charge ($B^-$) and a charge-balancing pharmaceutically acceptable cation ($M^+$) is present. A composition of this embodiment contains a compound of Formula II,

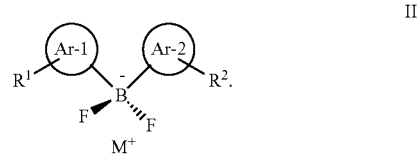

II

In another embodiment, a composition contains a compound of Formula III in which Ar-1 and Ar-2 are again as previously defined, $R^3$ is OH and $R^4$ is absent,

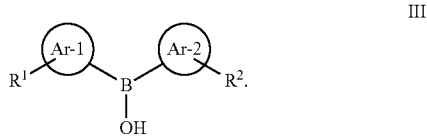

III

Yet another contemplated aspect of the invention is a method of inhibiting the phosphatase activity of a transmembrane receptor-like PTP (RPTP) that comprises the steps of contacting the RPTP with an effective RPTP phosphatase activity-inhibiting amount of a boron-containing compound of Formula IV, and maintaining said contact for as long a time period as desired to inhibit said phosphatase activity. In Formula IV, $R^6$ has a Hammett sigma

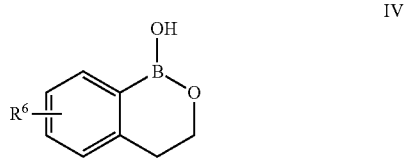

IV function value for a para and/or meta substituent, as appropriate, that is about −0.9 to about +0.08, preferably about −0.7 to about 0.00.

Illustrative results that generally correlate the Hammett sigma function values for para substituents in a compound of Formula IV are shown in Table 3, below, where $R^6$ is deemed para to the boron atom. Contrary to the trend observed for Formula I, II, and III, compounds of Formula IV exhibit more inhibitory activity with substituents having a more negative (less than zero) sigma value. Ring position numbers are shown below.

IV

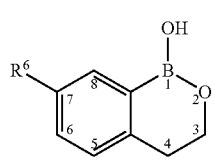

TABLE 3*

| Compound Number | $R^6$ | $\sigma_p$ value | LAR-ox Ki (µM) |
|---|---|---|---|
| S3 | m-F | 0.06 | 1000 |
| S4 | m- or p-H | 0.00 | 500 |
| S6 | m-(4-F—$C_6H_4$)C(O)NH | — | >1000 |
| B14 | m-$H_2$N | −0.66 | 57 |
| B5 | p-F | ?? | >1000 |

*Data obtained as discussed hereinafter.
m = meta;
p = para.

The substituents from which $R^6$ is chosen typically are amines such as amino, mono- and di-$C_1$-$C_6$-hydrocarbylamino, and cyclic amino having $C_5$-$C_7$-ring atoms, including the amino nitrogen atom such as N-pyrrolidinyl, N-morpholinyl, and N-piperidinyl groups and the like; straight, branched and cyclic $C_1$-$C_8$-hydrocarbyl groups such as methyl, ethyl, 2-ethylhexyl, allyl, but-3-en-2-yl, cyclopentyl, cyclohexyl, benzyl and phenyl groups and the like; and straight, branched and cyclic $C_1$-$C_8$-hydrocarbyloxy groups such as methoxy, ethoxy, allyloxy, but-3-en-2-yloxy, cyclopentyloxy, cyclohexyloxy, benzyloxy and phenyloxy groups and the like.

A pharmaceutical composition that contains an effective RPTP phosphatase activity-inhibiting amount of a boron-containing compound of Formula IV is also contemplated as discussed above and in detail below.

Pharmaceutical Composition

A compound of Formula I can be provided for use by itself, or as a salt, hydrate, or solvate thereof. As is well known, a hydrate is typically a solid form that contains one or more water molecules or a fraction of a water molecule as when one water molecule is shared by two molecules of a compound. A solvate is similar to a hydrate except that a water molecule is replaced by one or more or a fractional amount of a solvent molecule(s) other than water. A preferred salt form is a pharmaceutically acceptable salt.

Although substituent groups can provide an acid or base functionality, a contemplated compound of Formula I can be an acid and used in the form of a pharmaceutically acceptable base addition salt derived from an inorganic or organic base. Examples include salts with pharmaceutically acceptable alkali metals or alkaline earth metals, such as sodium, potassium, calcium or magnesium (inorganic bases) or with organic bases or basic quaternary ammonium salts.

The reader is directed to Berge, J. Pharm. Sci. 1977 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

A contemplated pharmaceutical composition contains an effective RPTP phosphatase activity-inhibiting amount of a boron-containing compound of one or more of Formulas I (II and III) and IV or a pharmaceutically acceptable salt thereof dissolved or dispersed in a physiologically tolerable carrier or diluent. Such a composition can be used to contact a RPTP phosphatase in vitro as in a cell culture, cell lysate or aqueous composition, and in vivo as in a living, host mammal, preferably in diagnosed need.

A contemplated composition is typically administered a plurality of times over a period of days. More usually, a contemplated composition is administered a plurality of times in one day, with several such dosings occurring over a period of several days. The biological activity-inhibiting amount of compound can therefore be present in a single dose, or can be achieved over a period of time through multiple contacts or administrations.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., Remington's Pharmaceutical Sciences, Mack Publishing Co., Easton, Pa., 1975, and Liberman, H. A. and Lachman, L., Eds., Pharmaceutical Dosage Forms, Marcel Decker, New York, N.Y., 1980.

An injectable preparation, for example, a sterile injectable aqueous or oleaginous suspension can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

A sterile solution can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a compound used in this invention is ordinarily combined with one or more excipients such as adjuvants appropriate to the indicated route of administration. If administered per os, the compounds can be admixed with lactose, sucrose, starch powder, cellulose esters of alkanoic acids, cellulose hydrocarbyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in diagnosed need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro contact is contemplated, a culture of cells from an illustrative mammal is often utilized, or the RPTP enzyme whose activity is to be inhibited can be present dissolved or suspended in an aqueous medium.

Preferably, the pharmaceutical composition is in unit dosage form. In such form, the composition is divided into unit doses containing appropriate quantities of the compound of Formula I. The unit dosage form can be a packaged preparation, the package containing discrete quantities of the preparation, for example, in vials or ampules.

Compound Syntheses

Another aspect of the invention contemplates the synthesis of an asymmetrically-substituted difluoroborate of Formula II, below,

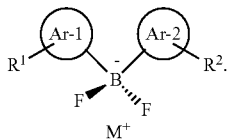

II

A contemplated method uses the steps of reacting an aryl boronic cyclic ester of Formula V-a or Formula V-b with an aryl Grignard reagent whose aryl group (Ar-2, $R^2$) is different from the first-named aryl group to form a diaryl-substituted boronic acid compound of Formula V-c. For an asymmetrically-substituted difluoroborate of Formula II, when Ar-1

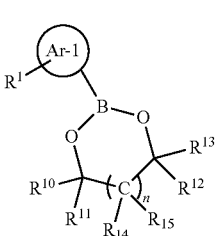

V-a

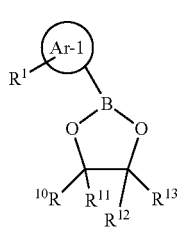

V-b and Ar-2 are the same, $R^1$ and $R^2$ are different to provide the asymmetrical substitution.

In Formulas V-a and V-b, $R^{10}$, $R^{11}$, $R^{12}$, $R^{13}$, $R^{14}$, and $R^{15}$ (collectively, $R^{10-15}$) are the same or different substituent that is a hydrogen or a $C_1$-$C_4$-hydrocarbyl group. Each of $R^{10-15}$ is preferably hydrogen.

In Formula V-a, n is one or zero, such that when n is zero, the parenthesized carbon atom shown in Formula V-a is absent as are both of $R^{14}$ and $R^{15}$ so that the depicted boron-containing ring becomes a 5-membered ring as is shown in Formula V-b. It is also preferred that n be zero.

The compound of Formula V-c so formed is

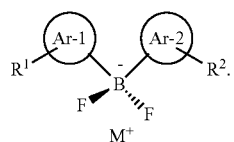

V-c reacted with a fluoridating agent to form the asymmetrically-substituted difluoroborate of Formula II, where $M^+$ is a a pharmaceutically acceptable cation

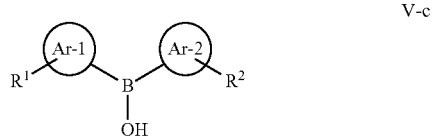

II

A number of fluorinating reagents are well-known in the art. Illustrative useful reagents include tetra-n-butylammonium fluoride, cesium fluoride or potassium fluoride in the presence of L-(+)-tartaric acid, $KHF_2$, $BF_3$, $BF_3Et_2O$, HF, $NH_4BF_4$ and $NaHF_2$. The cation, $M^+$, of a compound of Formula II is typically provided by the fluorinating reagent, rather than by an exchange reaction. Potassium hydrogenfluoride is a preferred fluorinating reagent.

An illustrative synthetic Reaction Scheme is shown below using preferred reagents.

Reaction Scheme

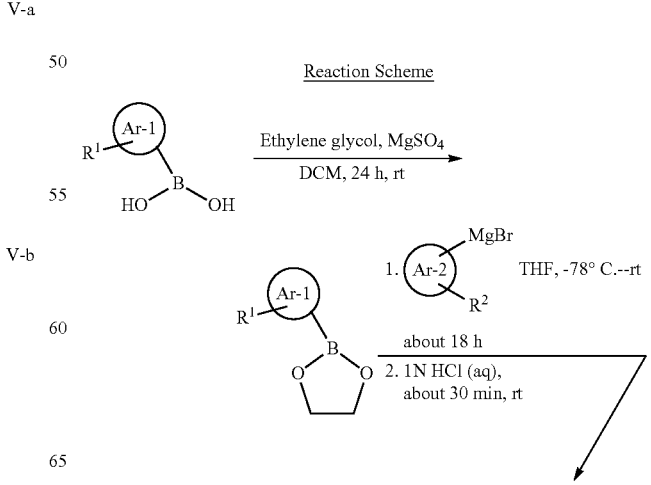

21

-continued

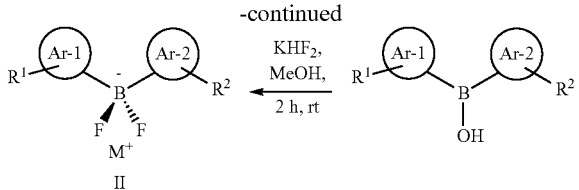

Results

Assay Results

A series illustrative assays were carried out using Compound CL-37 to inhibit the activity of several different PTPs in the oxidized form, including PTP1B. The results are shown in FIG. 1 in which it is clearly seen that the phosphatase activity of LAR and PTP-sigma are the most actively inhibited. Those two enzymes are in the same family of trans-membrane protein.

Under cellular condition, different PTPs have very different redox states depending on what biological function is being performed. This adds another level of specificity to the current approach because it can aim for specific biological processes with the appropriate oxidized protein level.

Leukocyte common antigen-related (LAR) and PTPσ were used as illustrative type IIa RPTPs in phosphorylation inhibition assays using several compounds of the invention and control compounds. The results of those assays, reported as inhibition constants, Ki in micromolar concentrations (μM), are shown in the Table below

| Compound Identification | Structure | LAR-oxidized Ki (μM) | PTPσ-oxidized Ki (μM) |
|---|---|---|---|
| CL-60 | MeO—⌬—B(F)(F)K⁺—⌬—OMe | >1000 | |
| CL-37 | ⌬—B(F)(F)K⁺—⌬ | 5 | 4 |
| CL-65 | F—⌬—B(F)(F)K⁺—⌬—F | 4 | |
| CL-61 | Cl—⌬—B(F)(F)K⁺—⌬—Cl | 4 | |
| CL-76 | Ph-⌬—⌬—B(F)(F)K⁺—⌬—F | 1 | |
| CL-83 | Ph-⌬—⌬—B(F)(F)K⁺—⌬—Cl | 3 | |

-continued
| Compound Identification | Structure | LAR-oxidized Ki (μM) | PTPσ-oxidized Ki (μM) |
|---|---|---|---|
| CL-30 | 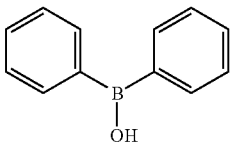 [SMILES: OB(c1ccccc1)c1ccccc1] | 20 | |
| CL-73-2 | 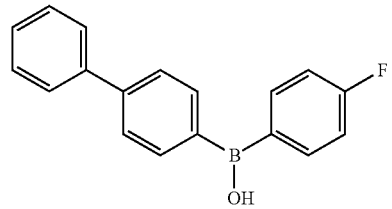 [SMILES: OB(c1ccc(F)cc1)c1ccc(-c2ccccc2)cc1] | 1 | |
| CL-82 | 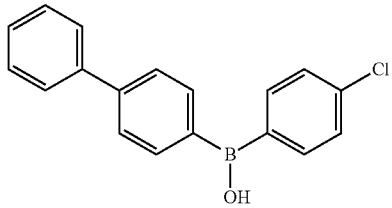 [SMILES: OB(c1ccc(Cl)cc1)c1ccc(-c2ccccc2)cc1] | 0.3 | |
| CL-49 | 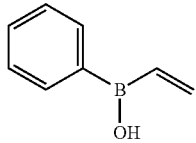 | >1000 | |
| S-3 | 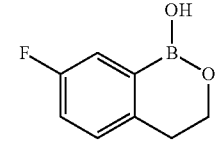 | 1000 | |
| S-4 | 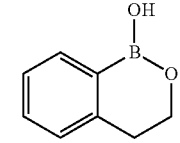 [SMILES: OB1OCCc2ccccc21] | 500 | |
| B-5 | 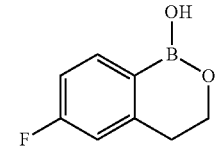 | >1000 | >1000 |
| S-6 | 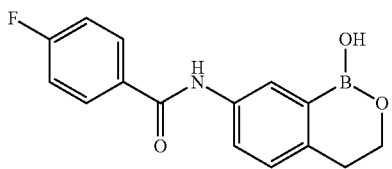 [SMILES: O=C(Nc1ccc2c(c1)B(O)OCC2)c1ccc(F)cc1] | >1000 | |

| Compound Indentification | Structure | LAR-oxidized Ki (μM) | PTPσ-oxidized Ki (μM) |
| --- | --- | --- | --- |
| B-14 | [structure: 7-amino benzoxaborole with OH] | 57 | 100 |
| B-7 | [structure: fluoro benzoxaborole with OH] | >1000 | >1000 |
| B-1 | [structure: benzoxaborole with OH] | >1000 | >1000 |
| B-2 | [structure: amino benzoxaborole with OH] | >1000 | >1000 |
| CL-70 | [structure: biphenyl trifluoroborate potassium salt] | >1000 | |

Stability of Difluoroborate Compounds Using $^{19}F$ and $^{11}B$ NMR

NMR is a useful tool for investigating compounds' stabilities owing to its high sensitivity. Here, we show an example of difluoroborate compounds' stability using the $^{19}F$ and $^{11}B$ NMR spectra of Compound CL-83 in deuterated acetonitrile alone and a mixture of deuterated acetonitrile and water (80% Acetonitrile-$d_3$ and 20% $D_2O$; about 11.1 mol/L of $D_2O$) with different incubation time (1 hour to seven days) at room temperature.

A signal was observed at 6.9 ppm in the $^{11}B$ NMR spectrum and one was observed at −159.3 ppm in the $^{19}F$ NMR spectrum when CL-83 was dissolved in deuterated acetonitrile. No new signals were detected in either the $^{19}F$ or the $^{11}B$ NMR spectra (scheme 1 and 2) when Compound CL-83 was dissolved in a mixture of deuterated acetonitrile and water with incubation times up to seven days at room temperature.

In other words, no hydrolysis or degradation of Compound CL-83 was observed in both conditions (with and without 20% $D_2O$). This suggests that the difluoroborates reported here are quite stable in aqueous conditions and ambient temperature.

Materials and Methods

General Information

Commercial solvents and reagents were used without further purification. Analytical thin-layer chromatography (TLC) was performed on Whatman® silica gel plates with fluorescence $F_{254}$ indicator and column chromatography was performed using the indicated solvent on Merck 60 silica gel (230-400 mesh).

$^1H$ NMR (300, 360, 400 and 500 MHz), $^{11}B$ NMR (160 MHz), $^{13}C$ NMR (100 and 125 MHz), and $^{19}F$ (470 MHz) NMR spectra were recorded on Bruker Avance™ III HD 500 and Bruker Avance™ 300, 360 and 400 spectrometers. Data for $^1H$ NMR are reported as follows: chemical shift (ppm), and multiplicity (s=singlet, d=doublet, t=triplet, q=quartet, quint=quintet, m=multiplet). Data for $^{13}C$ NMR are reported as ppm.

Compounds CL-13 [Benkovic et al., *J. Med. Chem.* 2005, 48, 7468-7476], CL-16 [Benkovic et al., *J. Med. Chem.* 2005, 48, 7468-7476], CL-37 [Ito et al., *Synlett*, 2003, 10, 1435-1438], and CL-70 [Gerbino et al., *Eur. J. Org. Chem.* 2009, 23, 3964-3972] were synthesized using procedures previously described in the corresponding references.

RPTP Assay

Standard Assay Conditions

Leukocyte common antigen-related (LAR) and PTPσ were used as illustrative type IIa RPTPs. Illustratively, purified LAR (100 nM) was mixed with $H_2O_2$ (2 mM) in phosphatase assay buffer (50 mM HEPES, pH 7.0, 100 mM NaCl, 0.1% BSA) at room temperature for 10 minutes. Excess $H_2O_2$ was removed with a Zeba™ Desalting Column (Thermo Scientific) equilibrated in the assay buffer without any reducing agent. Phosphatase activity was measured for each protein sample using 6,8-difluoro-4-methylumbiliferyl phosphate (DiFMUP) as the substrate, with or without 5 mM Tris(2-carboxyethyl)phosphine hydrochloride (TCEP). Activity of the oxidized sample was compared to that of the untreated (unoxidized) sample in the presence of 5 mM TCEP.

LAR-OX (10 nM) was incubated with compounds (0.1 mM) for varying lengths of time and the phosphatase activity was monitored using DiFMUP as substrate following reduction of the PTP with TCEP (5 mM). TCEP was not removed before adding DiFMUP. DiFMUP was added right after TCEP and the activity was followed continuously for 60 minutes. Activity can be recovered in the absence of the boron-containing compounds within the first 15 minutes. The above protocol was used to test the activity of other phosphatases (PTP1B, PTPσ, SHP2, PTPα, PTEN, and JSP1).

FIG. 1 shows that the strategy of using diarylborates to inhibit PTPs is highly selective. LAR and PTPσ (both RPTPs) are highly susceptible to this approach. One possible explanation is the difference in the stability of active site sulfenic acids found in different PTPs. Furthermore, different PTPs will have different redox states depending on the cellular condition and the biological function being performed. This might allow us to target specific biological processes based on specific protein oxidation level.

Muscle-Specific Kinase (MuSK)-Trapping Studies

C2C12 cells serum starved (8 hours) were stimulated with agrin (10 nM) for 30 minutes. Following stimulation, the cells were lysed 4° C. for 30 minutes.

About 1 mg of the lysate was incubated with Ni-NTA bound wild-type LAR (WT-LAR) or substrate-trapping mutant forms of LAR (DA-LAR or CS-LAR) at 4° C. for 90 minutes. Following this, beads were washed three times at 4° C.; first with lysis buffer followed by two more washes with wash buffer (PBS, pH 7.4, 0.05% BSA, 0.05% Tween®-20 and protease inhibitors). Complexes were separated by SDS-PAGE and immunoblotted using anti-MUSK antibody.

C2C12 cells serum starved (8 hours) and then treated with CL-37 for 1 hour. Following which, cells were stimulated with Agrin (10 nM) for varying lengths of time (0-60 minutes). The cells were lysed and lysates were used to immunoprecipitate tyrosine phosphorylated proteins using 4G10® (05-321 from EMD Milliooire Corp. and PY20 (such as ab10321 fromabcam Plc) antibodies for 90 minutes at 4 C. The immunocomplexes were washed and resolved on SDS gels and immunoblotted using anti-MUSK antibody.

For the immunoprecipation experiments, 1 mg of total cell lysate was incubated with anti-pTyr antibodies at 4° C. for 90 minutes. The interacting protein complexes were immunoprecipitated after incubating the lysate-antibody mixture with protein A/G Sepharose® at 4° C. for 30 minutes. After immunoprecipitation, Sepharose® beads were washed three times at 4° C. with wash buffer (PBS, pH 7.4, 0.05% BSA, 0.05% Tween®-20 and protease inhibitors). Complexes were separated by SDS-PAGE and immunoblotted using anti-MUSK antibody.

Figure 2:
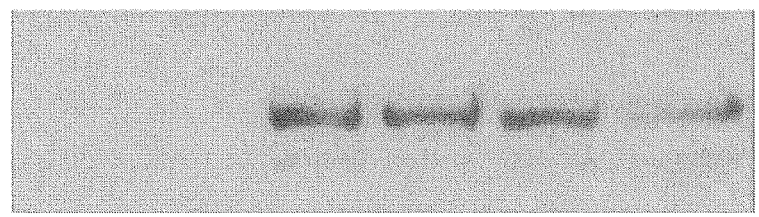
FIG. 2 contains three photographic panels of a series of SDS gels in which agrin-stimulated (10 nM) lysates from C2C12 myotubes were incubated with wild type-LAR (WT-LAR) or substrate-trapping mutant forms of LAR (DA-LAR or CS-LAR) and immunocomplexes were resolved on SDS gels and immunoblotted using anti-MuSK antibody (upper panel). The middle panel shows the MuSK left untrapped by the trapping mutants in the supernatant and the lower panel indicates equal loading and equal expression of MuSK in all three samples.
Figure 2:
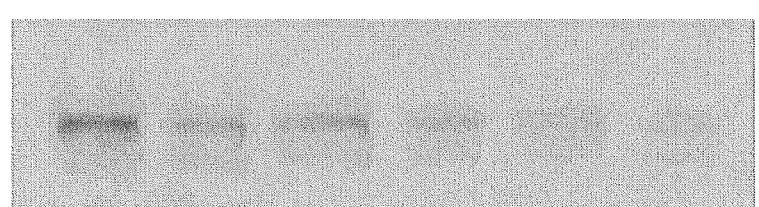
Figure 2:
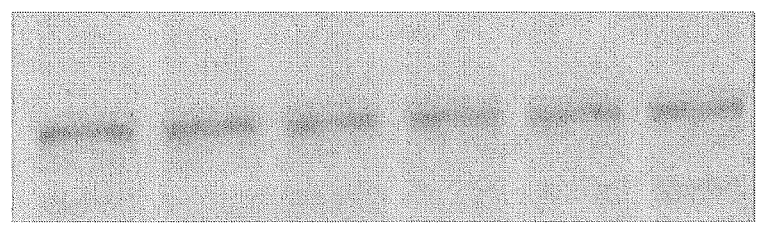

To further demonstrate the utility of the disclosed boron-based inhibitors, a cell based assay was conducted. FIG. 2 shows the ability to use Agrin (a proteoglycan) to induce the oxidation of LAR. An oxidized LAR is inactive and cannot dephosphorylate MuSK. However, in the absence of boron inhibitor, oxidized wild type LAR can be readily reduced back to its active reduced form and carry out the dephosphorylation of MuSK.

Figure 3:
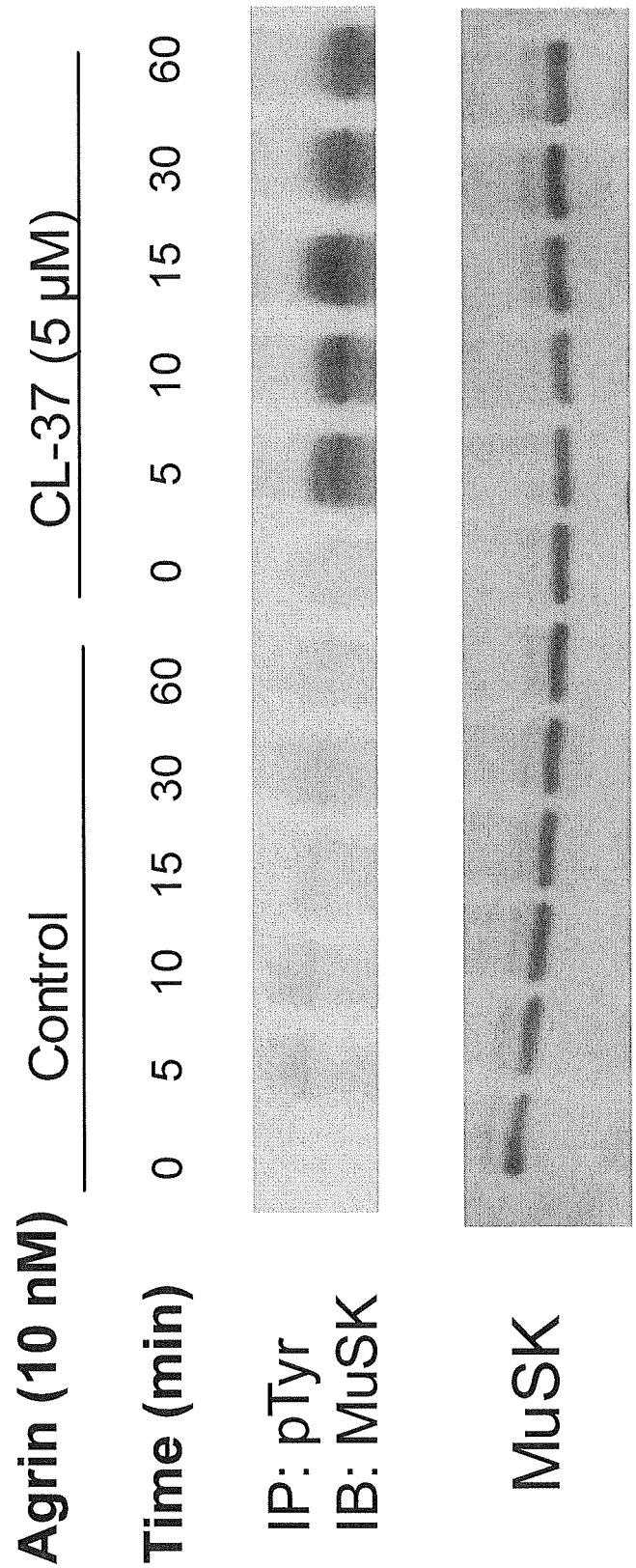
FIG. 3 contains two photographic panels of a series of SDS gels in which C2C12 myotubes were stimulated for various time periods (0-60 minutes) with Agrin (10 nM). The cells were lysed and lysates were used to immunoprecipitate tyrosine phosphorylated proteins using 4G10 and PY20 antibodies for 90 minutes at 4 C. The immunocomplexes were washed, resolved on SDS gels and immunoblotted using anti-MuSK antibody and illustrates that Compound CL-37 inhibits LAR from dephosphorylating MuSK.
Figure 4:
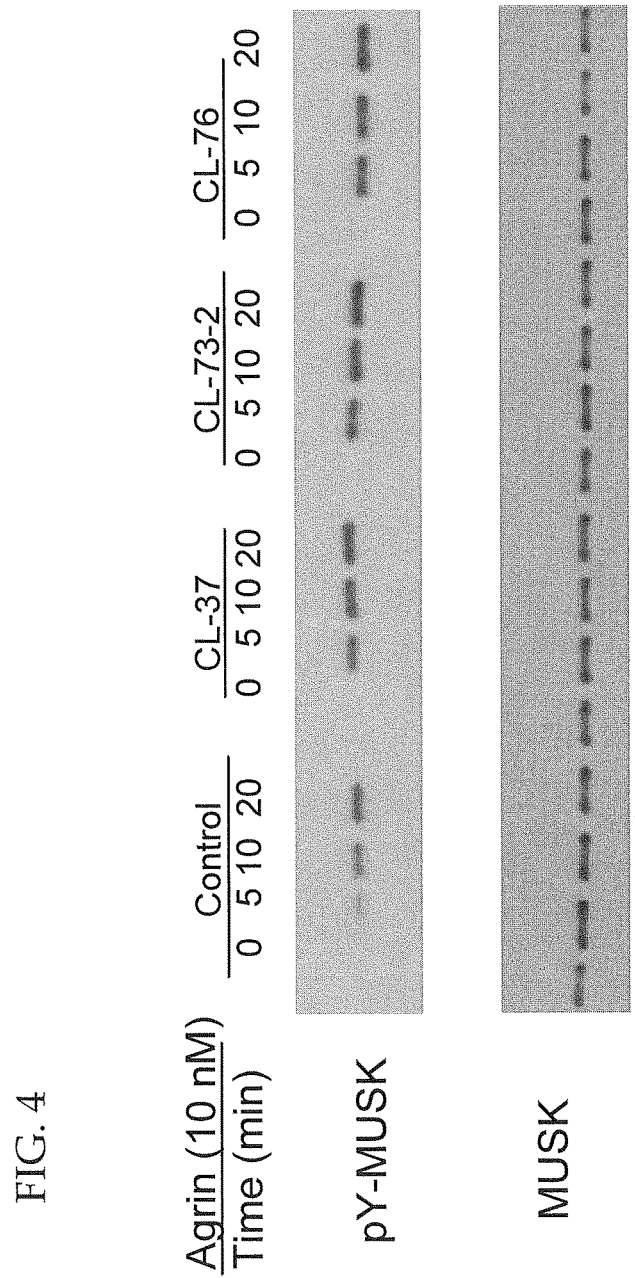
FIG. 4 shows results of a study similar to that of FIG. 3, except that each of Compounds CL-37, CL-76 and CL-73-2 was utilized and each is seen to enhance the phosphorylation level of MUSK (relative to the control) in response to agrin stimulation

In contrast, FIG. 3 illustrates that in the presence of boron inhibitor CL-37 (5 μM), the phosphorylation level of MuSK is significantly higher than the control (absence of CL-37). This demonstrates the ability of CL-37 to inhibit LAR by trapping the oxidized LAR. Again, oxidized LAR is the inactive form and it cannot dephosphorylate MuSK. It should also be pointed out that under the experimental condition, CL-37 did not exhibit an adverse effect on cell vitality. Similar higher phosphorylation results of MuSK are shown in FIG. 4 in which each of CL-37, CL-76 and CL-73-2 was used in an assay similar to that of FIG. 3.

Compound Syntheses

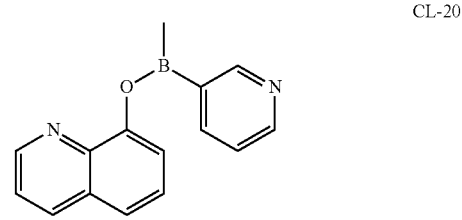 [SMILES: CB(Oc1cccc2cccnc12)c1cccnc1]

CL-20

Isopropyl magnesium chloride (2.5 mL, 2 M in THF) was added to a solution of 3-bromopyridine (790 mg, 5 mmol) in anhydrous THF (7.5 mL) under argon atmosphere at 0° C. The resulting mixture was stirred at room temperature (r.t.) for 1 hour, then the reaction mixture was cooled to −78° C. and diisopropyl methyl borane was added dropwise via syringe. The resulting mixture was stirred at −70° C. for about one-half hour, then stirred at r.t. overnight (about 18 hours). 50 mL THF was added to dilute the reaction mixture, which was then washed with saturated NaCl (aq) and extracted with ethyl acetate (EA). The organic layers were combined and dried over magnesium sulfate. Solvent was then removed in vacuo, giving crude borinic acid, which was dissolved in anhydrous ethanol (8 mL).

8-Hydroxyquinoline (725.8 mg, 5 mmol) was added, and the resulting mixture was stirred at 40° C. for 30 minutes. Solvent was removed under reduced pressure, resulting in oil residue, which was recrystallized in diethyl ether and hexane, giving CL-20 (340 mg, 27%) as yellow solid.

$^1$H NMR (360 MHz, Aceton-$d_6$) δ (ppm) 9.00 (d, J=5.0 Hz, 1H), 8.73 (d, J=8.4 Hz, 1H), 8.58 (s, 1H), 8.35 (dd, J=4.8, 1.7 Hz, 1H), 7.87 (dd, J=5.0, 5.0 Hz, 1H), 7.71-7.66 (m, 2H), 7.39 (d, J=8.4 Hz, 1H), 7.18 (dd, J=7.5, 4.8 Hz, 1H), 7.11 (d, J=7.6 Hz, 1H), 0.39 (s, 3H). $^{13}$C NMR (90 MHz, Aceton-$d_6$) δ (ppm) 159.6, 153.0, 148.7, 140.6, 140.0, 138.8, 137.8, 133.3, 129.5, 124.6, 123.7, 113.2, 109.4, 7.7.

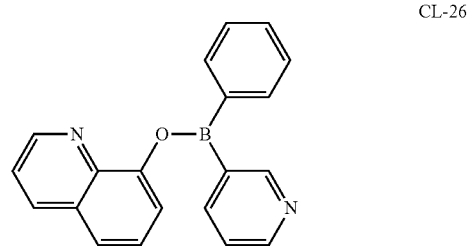 [SMILES: c1ccc(B(Oc2cccc3cccnc23)c2cccnc2)cc1]

CL-26

This substance was prepared starting with phenylboronic acid 1,2-ethanediol ester and thereafter using the same procedure employed for the preparation of CL-20. The yield was 23%.

$^1$H NMR (400 MHz, DMSO-d$_6$) δ (ppm) 9.24 (d, J=4.5 Hz, 1H), 8.80 (d, J=8.0 Hz, 1H), 8.56 (s, 1H), 8.39 (dd, J=4.8, 1.7 Hz, 1H), 7.92 (dd, J=5.0, 5.0 Hz, 1H), 7.74-7.69 (m, 2H), 7.45 (d, J=8.3 Hz, 1H), 7.38-7.36 (m, 2H), 7.24-7.18 (m, 5H). $^{13}$C NMR (100 MHz, DMSO-d$_6$) δ (ppm) 157.6, 152.4, 147.8, 141.5, 140.1, 139.0, 136.2, 132.4, 131.3, 127.9, 127.4, 126.7, 124.2, 123.0, 113.2, 109.0.

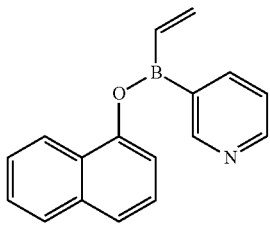

CL-28

Anhydrous magnesium sulfate (1 g) was added to a solution of (3-pyridyl)vinyl borinic acid [Sanders et al., U.S. Pat. Appl. Publ. 2007, US 20070286822 A1] (650 mg, 4.9 mmol) and 1-naphthalenol (773 mg, 5.4 mmol) in benzene (10 mL). The resulting mixture was kept refluxing overnight (about 18 hours). The reaction mixture was then cooled to room temperature, and the solvent removed in vacuo. This process yielded a crude product, which was purified by silica gel column chromatography (1/1/1, Hexane/EtOAc/Acetone), resulting in Compound CL-28 (60 mg, 5%) as a colorless oil.

$^1$H NMR (360 MHz, CDCl$_3$) δ (ppm) 8.87 (d, J=5.2 Hz, 2H), 8.10 (t, J=7.7 Hz, 1H), 7.68 (t, J=6.9 Hz, 2H), 6.06-6.03 (m, 6H), 5.88-5.83 (m, 3H). $^{13}$C NMR (100 MHz, CDCl$_3$) δ (ppm) 154.4, 143.9, 143.8, 141.1, 139.3, 131.6, 131.5, 131.4, 125.7, 125.6, 125.4.

General Procedure a for the Preparation of Potassium Difluorodiaryl Borate.

2-Aminoethoxydiaryl borinate was dissolved in a 1:1 mixture of MeOH/Acetone and an equivalent volume of aqueous HCl (1 M) was added dropwise. The resulting mixture was stirred at room temperature for two hours, then extracted with EtOAc, dried over anhydrous MgSO$_4$ and concentrated in vacuo to yield the corresponding pure borinic acid. To the solution of the borinic acid in methanol, was added KHF$_2$ (1 eq) at room temperature, and the suspension was left to stir at room temperature until the KHF$_2$ was dissolved completely (about 2 hours). All volatiles were removed in vacuo. The resulting residue was dissolved in acetone and undissolved solids were removed by filtration. Acetone was removed in vacuo to yield potassium difluorodiaryl borate as colorless solid.

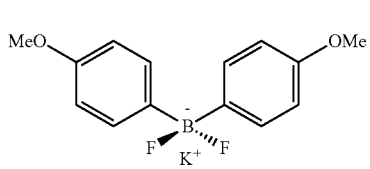

CL-60

Following the general procedure, the 2-aminoethoxydiaryl borinate of the title compound is known and fully described [Benkovic et al., *J. Med. Chem.* 2005, 48, 7468-7476]. The overall yield of C-60 was 71%.

$^1$H NMR (400 MHz, CD$_3$CN) δ (ppm) 7.30 (d, J=7.9 Hz, 4H), 6.71 (d, J=7.9 Hz, 4H), 3.71 (s, 6H). $^{13}$C NMR (125 MHz, CD$_3$CN) δ (ppm) 158.0, 133.3 (J$_{C,F}$=10.7 Hz), 112.9, 55.3. $^{11}$B NMR (160 MHz, CD$_3$CN) δ (ppm) 7.4 (br s). $^{19}$F NMR (470 MHz, CD$_3$CN) δ (ppm) −156.7.

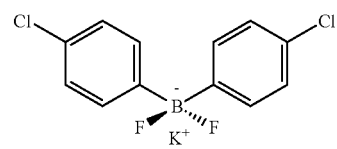

CL-61

Following the general procedure, the 2-aminoethoxydiaryl borinate of the title compound is known and fully described [Benkovic et al., *J. Med. Chem.* 2005, 48, 7468-7476]. The overall yield of CL-61 was 86%.

$^1$H NMR (500 MHz, CD$_3$CN) δ (ppm) 7.38 (d, J=9.7 Hz, 4H), 7.13 (d, J=9.7 Hz, 4H). $^{13}$C NMR (125 MHz, CD$_3$CN) δ (ppm) 134.0 (J$_{C,F}$=3.5 Hz), 130.8, 127.2. $^{11}$B NMR (160 MHz, CD$_3$CN) δ (ppm) 6.7 (br s). $^{19}$F NMR (470 MHz, CD$_3$CN) δ (ppm) −159.4.

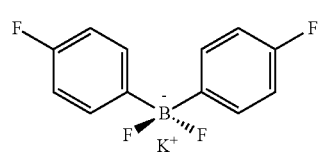

CL-65

Following the general procedure, the 2-aminoethoxydiaryl borinate of the title compound is known and fully described [Benkovic et al., *J. Med. Chem.* 2005, 48, 7468-7476]. The overall yield of CL-65 was 85%.

$^1$H NMR (400 MHz, DMSO-d$_6$) δ (ppm) 7.28 (t, J=5.6 Hz, 4H), 6.80 (t, J=7.0 Hz, 4H). $^{13}$C NMR (125 MHz, DMSO-d$_6$) δ (ppm) 161.9 (d, J$_{C,F}$=236.8 Hz), 133.4 (m), 113.4 (d, J$_{C,F}$=18.5 Hz). $^{11}$B NMR (160 MHz, CD$_3$CN) δ (ppm) 6.2 (br s). $^{19}$F NMR (470 MHz, CD$_3$CN) δ (ppm) −120.1 (2F), −155.5 (2F).

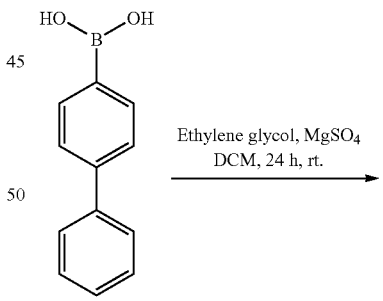

Ethylene glycol, MgSO$_4$
DCM, 24 h, rt.

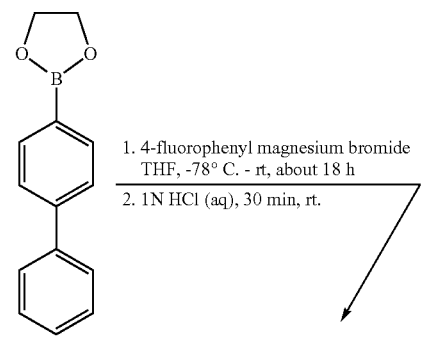

1. 4-fluorophenyl magnesium bromide
   THF, -78° C. - rt, about 18 h
2. 1N HCl (aq), 30 min, rt.

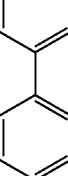

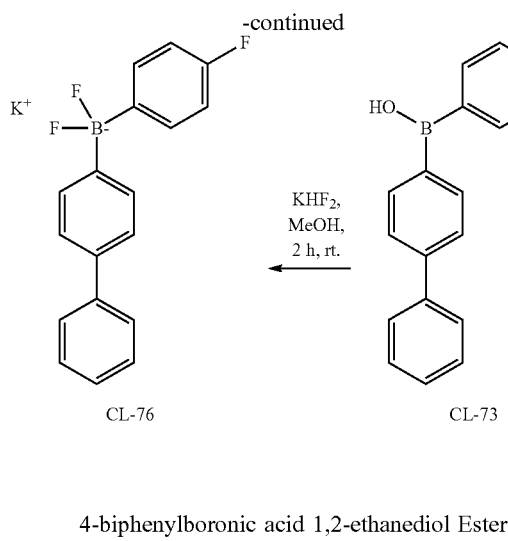

CL-76              CL-73

4-biphenylboronic acid 1,2-ethanediol Ester

To a solution of 4-biphenylboronic acid (2 g, 10 mmol) in DCM (10 mL) was added anhydrous magnesium sulfate (2 g) and ethylene glycol (0.620 g, 10 mmol). The reaction mixture was stirred for 20 hours at room temperature. The reaction mixture was filtered, washed with DCM, and concentrated in vacuo to give 2.2 g (98%) of product, which was used without purification.

$^1$H NMR (360 MHz, CDCl$_3$) δ (ppm) 7.90 (d, J=8.0 Hz, 2H), 7.64 (d, J=7.9 Hz, 4H), 7.46 (t, J=7.5, 2H), 7.37 (t, J=7.4 Hz, 1H), 4.41 (s, 4H).

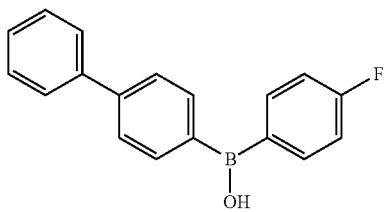

CL-73-2

To a solution of 4-biphenylboronic acid 1,2-ethanediol ester (2.2 g, 9.8 mmol) was added 4-fluorophenylmagnesium bromide (9.8 mL, 1M in THF, 9.8 mmol) at −78° C. The resulting mixture was stirred at −78° C. for about 30 minutes, then stirred at r.t. overnight (about 18 hours). 50 mL THF was added to dilute the reaction mixture, that was then washed with saturated NaCl(aq) and extracted with EA. The organic layers were combined and dried over magnesium sulfate. Solvent was removed in vacuo, giving crude borinic acid, which was purified by silica gel column chromatography (3/1 Hexane/EtOAc) resulting in CL-73 (960 mg, 36%) as a colorless solid.

$^1$H NMR (500 MHz, CDCl$_3$) δ (ppm) 7.86 (t, J=8.4 Hz, 4H), 7.71 (d, J=7.3 Hz, 2H), 7.67 (d, J=6.7 Hz, 2H), 7.49 (t, J=6.8 Hz, 2H), 7.40 (t, J=6.9 Hz, 1H), 7.16 (t, J=7.9 Hz, 2H). $^{13}$C NMR (125 MHz, CDCl$_3$) δ (ppm) 165.2 (d, J$_{C,F}$=249.7 Hz), 143.9, 140.9, 137.4 (d, J$_{C,F}$=8.1 Hz), 135.1, 129.0, 127.9, 127.4, 126.9, 115.2 (d, J$_{C,F}$=19.9 Hz). $^{11}$B NMR (160 MHz, CDCl$_3$) δ (ppm) 45.0 (br s). $^{19}$F NMR (470 MHz, CDCl$_3$) δ (ppm) −108.4.

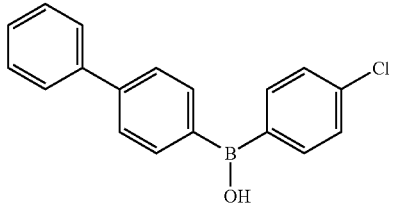

CL-76

Following the general procedure starting with borinic acid Compound CL-73, the yield of Compound CL-76 was 96%.
$^1$H NMR (500 MHz, CD$_3$CN) δ (ppm) 7.61 (d, J=7.3 Hz, 2H), 7.49 (d, J=8.0 Hz, 2H), 7.45-7.39 (m, 6H), 7.28 (t, J=7.3 Hz, 1H), 6.86 (t, J=9.0 Hz, 2H). $^{13}$C NMR (125 MHz, CD$_3$CN) δ (ppm) 162.1 (d, J$_{C,F}$=237.7 Hz), 143.2, 137.8, 133.7 (m), 132.9 (m), 129.6, 127.5, 127.3, 126.0, 113.6 (d, J$_{C,F}$=18.6 Hz). $^{11}$B NMR (160 MHz, CD$_3$CN) δ (ppm) 6.2 (br s). $^{19}$F NMR (470 MHz, CD$_3$CN) δ (ppm) −121.5 (1F), −158.7 (2F).

CL-82

This substance was prepared starting with 4-biphenylboronic acid 1,2-ethanediol ester and 4-chlorophenylmagnesium bromide using the same procedure employed for the preparation of Compound CL-73. The yield was 69%.
$^1$H NMR (500 MHz, CDCl$_3$) δ (ppm) 7.85 (d, J=7.8 Hz, 2H), 7.80 (d, J=8.1 Hz, 2H), 7.70 (d, J=4.9 Hz, 2H), 7.66 (d, J=7.4 Hz, 2H), 7.50-7.44 (m, 4H), 7.40 (t, J=7.3 Hz, 1H). $^{13}$C NMR (125 MHz, CDCl$_3$) δ (ppm) 144.0, 140.8, 137.7, 136.4, 135.2, 129.0, 128.4, 127.9, 127.4, 126.9. $^{11}$B NMR (160 MHz, CDCl$_3$) δ (ppm) 45.0 (br s).

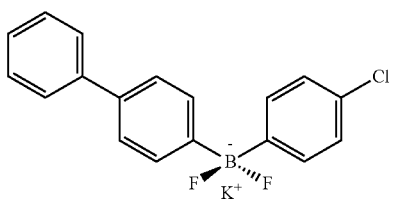

CL-83

This substance was prepared starting with Compound CL-82 and using the same procedure employed for the preparation of CL-76. The yield was 97%.
$^1$H NMR (500 MHz, CD$_3$CN) δ (ppm) 7.61 (d, J=7.3 Hz, 2H), 7.50 (d, J=7.7 Hz, 2H), 7.45-7.39 (m, 6H), 7.29 (t, J=7.3 Hz, 1H), 7.15 (d, J=7.9 Hz, 2H). $^{13}$C NMR (125 MHz, CD$_3$CN) δ (ppm) 143.1, 138.0, 134.0, 132.9, 130.7, 129.6, 127.5, 127.4, 127.2, 126.1. $^{11}$16 NMR (160 MHz, CD$_3$CN) δ (ppm) 6.9 (br s). $^{19}$F NMR (470 MHz, CD$_3$CN) δ (ppm) −159.3 (2F).

Preparation of Compounds S3, S4, S6, and B14

Compounds S4, S6, and B14 were prepared by following the published procedures [Tomsho et al., *ACS Med. Chem.*

Lett. 2012, 3, 48-52; Zhou et al., U.S. Pat. No. 9,346,834 B2]. Compound S3 was obtained by following a similar procedure as described in the above citations. The synthetic steps are listed below.

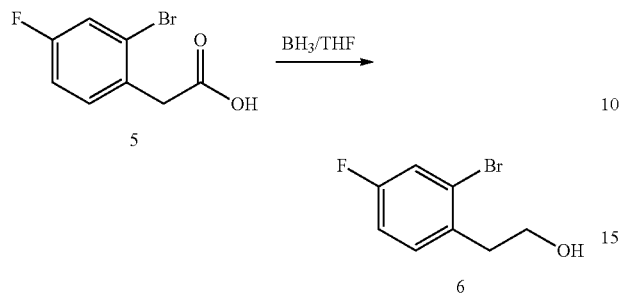

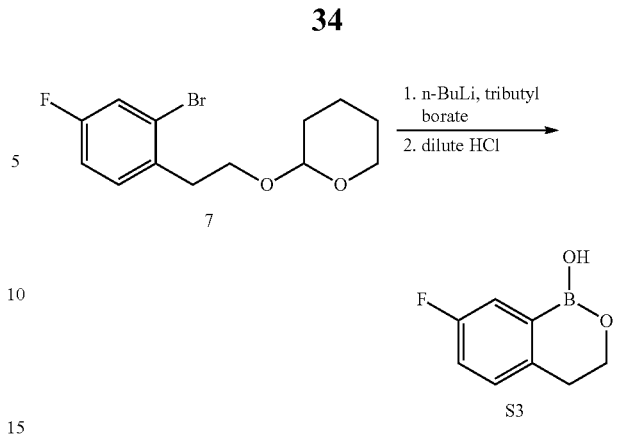

To a solution of Compound 5 (5.00 g, 21.46 mmol, 1.00 eq) in THF (50.00 mL) was added a solution of $BH_3 \cdot THF$ (1 M, 64.38 mL, 3.00 eq) in drop-wise at 0° C. under $N_2$. The reaction mixture was stirred at 25° C. for 1 hour. The reaction mixture was quenched by the addition MeOH (20 mL), and then diluted with $H_2O$ (20 mL) and extracted with EA (50 mL, 3 times). The combined organic layers were washed with brine (20 mL, 3 times), dried over anhydrous $Na_2SO_4$, filtered and concentrated under reduced pressure to give a residue. The residue was purified by column chromatography ($SiO_2$, PE:EA=20:1 to 3:1) to provide the product Compound 6 (4.50 g, 20.54 mmol, 95.71% yield) as yellow oil.

$^1H$ NMR (400 MHz; $CDCl_3$) δ (ppm) 7.33-7.29 (m, 1H), 7.27-7.27 (m, 1H), 7.26 (s, 1H), 6.99-6.74 (m, 1H), 3.95-3.86 (m, 2H), 2.96-2.88 (m, 2H).

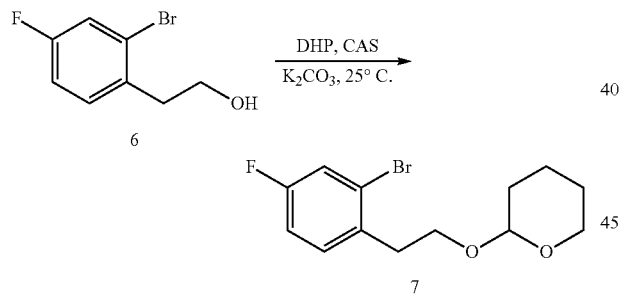

To a mixture of Compound 6 (2.00 g, 9.13 mmol, 1.00 eq) in DCM (20 mL) was added DHP (1.15 g, 13.70 mmol, 1.25 mL, 1.50 eq) and CSA (42.42 mg, 182.60 umol, 0.02 eq) in one portion at 25° C. The mixture was stirred at 25° C. for 2 hours. The mixture was admixed with $K_2CO_3$ (126.19 mg, 913.00 μmol, 0.10 eq) at 25° C. for 30 minutes. The mixture was filtered to remove the solids, and the filtrate was washed with $H_2O$ (20 mL) followed by brine wash (20 mL). The organic phase was dried over anhydrous $Na_2SO_4$, filtered and the filtrate was concentrated under reduced pressure. The residue was purified by column chromatography ($SiO_2$, PE:EA=100:1 to 10:1) to provide the product Compound 7 (2.10 g, crude) as light yellow oil.

$^1H$ NMR (400 MHz; $CDCl_3$) δ (ppm) 7.32-7.27 (m, 2H), 7.01-6.98 (m, 1H), 4.61 (q, J=4.0 Hz, 1H), 3.95-3.93 (m, 1H), 3.91-3.79 (m, 1H), 3.66-3.64 (m, 1H), 3.63-3.50 (m, 1H), 3.04 (t, J=7.2 Hz, 2H), 1.83-1.71 (m, 1H), 1.60-1.59 (m, 1H), 1.58-1.55 (m, 4H).

To a solution of Compound 7 (2.00 g, 6.60 mmol, 1.00 eq) in THF (20 mL) at −78 C was slowly added n-BuLi (2.5 M, 2.64 mL, 1.00 eq) under nitrogen atmosphere. The reagent tributyl borate (1.52 g, 6.60 mmol, 1.79 mL, 1.00 eq) was added at −78° C. The mixture was allowed to gradually warm to 25° C. with stirred for 12 hours. After carefully adding HCl (20 mL, 6 M), the mixture was stirred at 25° C. for another 1 hour. The reaction mixture was diluted with $H_2O$ (20 mL) and extracted with EA (30 mL, 3 times). The combined organic layers were washed with brine (30 mL, 2 times), dried over anhydrous $Na_2SO_4$, filtered and concentrated under reduced pressure to give a residue. The residue was purified by pre-HPLC to provide product Compound S3 (400.00 mg, 2.39 mmol, 36.21% yield, 99% purity) as a white solid after removing all the liquid.

$^1H$ NMR (400 MHz; DMSO) δ (ppm) 7.40 (dd, J=8.6, 2.6 Hz, 1H), 7.13-7.07 (m, 2H), 4.36 (br.s, 1H), 4.19 (t, J=6.0 Hz, 2H), 2.904 (t, J=6.0 Hz, 2H). LCMS: (M+H$^+$; m/z): 167.1.

Each of the patents, patent applications and articles cited herein is incorporated by intended to include one or more.

The foregoing description and the examples are intended as illustrative and are not to be taken as limiting. Still other variations within the spirit and scope of this invention are possible and will readily present themselves to those skilled in the art.

The invention claimed is:

1. A compound of Formula IIIb, wherein $R^1$ is phenyl and $R^2$ is a substituent selected from

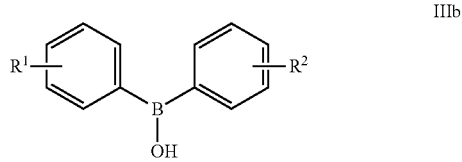

IIIb one or more of the group consisting of halogen, $C_1$-$C_6$-hydrocarbyl, trifluoromethyl, and nitro, and wherein the sum of Hammett sigma function values for para and/or meta substituents of the $R^1$ and $R^2$ substituents as appropriate is greater than about zero.

2. The compound according to claim 1, wherein $R^2$ is halogen.

3. The compound according to claim 1, wherein said compound has a structural formula shown below
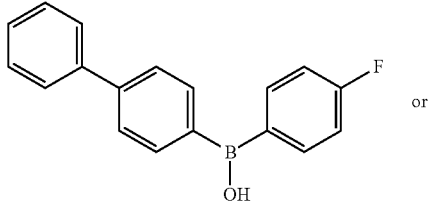
or
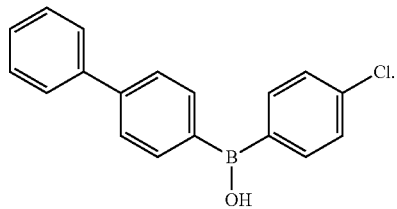
4. A compound of the structural Formula below
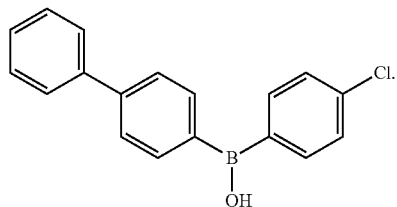 [SMILES: OB(c1ccc(Cl)cc1)c1ccc(-c2ccccc2)cc1]
5. A compound of the structural Formula below
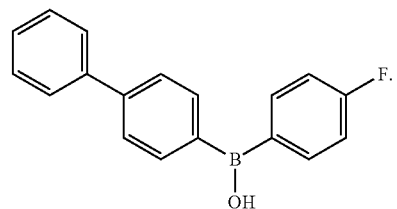 [SMILES: OB(c1ccc(F)cc1)c1ccc(-c2ccccc2)cc1]
* * * * *